US010451630B2

(12) United States Patent
Salafsky et al.

(10) Patent No.: US 10,451,630 B2
(45) Date of Patent: *Oct. 22, 2019

(54) SYSTEMS AND METHODS FOR HIGH THROUGHPUT ANALYSIS OF CONFORMATION IN BIOLOGICAL ENTITIES

(71) Applicant: Biodesy, Inc., South San Francisco, CA (US)

(72) Inventors: Joshua Salafsky, San Francisco, CA (US); Louis J. Dietz, Mountain View, CA (US); Ray Hebert, Florence, OR (US); Dar Bahatt, Foster City, CA (US)

(73) Assignee: BIODESY, INC., South San Francisco, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 15/965,577

(22) Filed: Apr. 27, 2018

(65) Prior Publication Data

US 2018/0340940 A1    Nov. 29, 2018

Related U.S. Application Data

(63) Continuation of application No. 14/754,465, filed on Jun. 29, 2015, now Pat. No. 9,989,534.

(Continued)

(51) Int. Cl.
*G02B 5/04* (2006.01)
*B01L 3/00* (2006.01)
(Continued)

(52) U.S. Cl.
CPC ........ *G01N 33/6845* (2013.01); *B01L 3/5085* (2013.01); *B01L 3/502715* (2013.01); *G01N 21/552* (2013.01); *G01N 21/636* (2013.01); *G01N 33/54366* (2013.01); *G01N 33/54373* (2013.01); *B01L 2300/0636* (2013.01); *B01L 2300/0819* (2013.01); *G02B 5/04* (2013.01); *G02B 5/045* (2013.01)

(58) Field of Classification Search
None
See application file for complete search history.

(56) References Cited

U.S. PATENT DOCUMENTS 5,145,790 A    9/1992    Mattingly et al.
5,156,810 A    10/1992   Ribi
(Continued)

FOREIGN PATENT DOCUMENTS

CA    2604099 C    2/2011
EP    0740156 A1    10/1996
(Continued)

OTHER PUBLICATIONS

European search report with written opinion dated Mar. 1, 2018 for EP Application No. 15815993.
(Continued)

*Primary Examiner* — Erik B Crawford
(74) *Attorney, Agent, or Firm* — Wilson Sonsini Goodrich & Rosati

(57) ABSTRACT

Methods, devices, and systems are disclosed for performing high throughput analysis of conformational change in biological molecules or other biological entities using surface-selective nonlinear optical detection techniques.

18 Claims, 25 Drawing Sheets

Related U.S. Application Data

(60) Provisional application No. 62/019,285, filed on Jun. 30, 2014.

(51) Int. Cl.
    *G01N 33/68*     (2006.01)
    *G01N 21/552*     (2014.01)
    *G01N 21/63*     (2006.01)
    *G01N 33/543*     (2006.01)

(56) References Cited

U.S. PATENT DOCUMENTS

| | | |
|---|---|---|
| 5,236,826 A | 8/1993 | Marshall |
| 5,376,556 A | 12/1994 | Tarcha et al. |
| 5,633,724 A | 5/1997 | King et al. |
| 5,696,157 A | 12/1997 | Wang et al. |
| 5,738,825 A | 4/1998 | Rudigier et al. |
| 5,800,992 A | 9/1998 | Fodor et al. |
| 5,962,248 A | 10/1999 | Tadano et al. |
| 6,055,051 A | 4/2000 | Eisenthal |
| 6,096,497 A | 8/2000 | Bauer |
| 6,180,415 B1 | 1/2001 | Schultz et al. |
| 6,187,247 B1 | 2/2001 | Buzzell et al. |
| 6,194,222 B1 | 2/2001 | Buechler et al. |
| 6,204,067 B1 | 3/2001 | Simon et al. |
| 6,228,326 B1 | 5/2001 | Boxer et al. |
| 6,284,197 B1 | 9/2001 | Abbott et al. |
| 6,410,245 B1 | 6/2002 | Northrop et al. |
| 6,455,303 B1 | 9/2002 | Orwar et al. |
| 6,456,423 B1 | 9/2002 | Nayfeh et al. |
| 6,699,719 B2 | 3/2004 | Yamazaki et al. |
| 6,780,584 B1 | 8/2004 | Edman et al. |
| 6,882,420 B2 | 4/2005 | Rassman et al. |
| 6,953,694 B2 | 10/2005 | Salafsky et al. |
| 7,023,547 B2 | 4/2006 | Venkatasubbarao et al. |
| 7,105,310 B1 | 9/2006 | Gray et al. |
| 7,108,970 B2 | 9/2006 | Levinson |
| 7,126,688 B2 | 10/2006 | Rassman et al. |
| 7,193,711 B2 | 3/2007 | Rassman et al. |
| 7,233,391 B2 | 6/2007 | Schermer et al. |
| 7,545,494 B2 | 6/2009 | Haiml et al. |
| 7,545,501 B2 | 6/2009 | Muraishi et al. |
| 7,709,808 B2 | 5/2010 | Reel et al. |
| 8,039,270 B2 | 10/2011 | Dultz et al. |
| 8,062,900 B2 | 11/2011 | Modavis |
| 8,139,288 B2 | 3/2012 | Osborne et al. |
| 8,355,133 B2 | 1/2013 | Dultz et al. |
| 8,497,073 B2 | 7/2013 | Salafsky |
| 8,932,822 B1 | 1/2015 | Salafsky |
| 2002/0030894 A1 | 3/2002 | Volcker et al. |
| 2003/0129649 A1 | 7/2003 | Kobilka et al. |
| 2003/0175160 A1 | 9/2003 | Archibald et al. |
| 2003/0205681 A1 | 11/2003 | Modlin |
| 2004/0146460 A1 | 7/2004 | Salafsky |
| 2005/0148063 A1 | 7/2005 | Cracauer et al. |
| 2007/0178012 A1 | 8/2007 | Ferrante et al. |
| 2010/0068144 A1 | 3/2010 | Salafsky |
| 2010/0323105 A1 | 12/2010 | Hosoe |
| 2012/0202296 A1 | 8/2012 | Eisenthal |
| 2013/0129628 A1 | 5/2013 | Pantazis |
| 2014/0113312 A1 | 4/2014 | Salafsky et al. |
| 2015/0051110 A1 | 2/2015 | Salafsky et al. |
| 2015/0377900 A1 | 12/2015 | Salafsky et al. |

FOREIGN PATENT DOCUMENTS

| | | |
|---|---|---|
| EP | 0941474 B1 | 3/2006 |
| EP | 1798555 A1 | 6/2007 |
| WO | WO-02095070 A2 | 11/2002 |
| WO | WO-03055379 A2 | 7/2003 |
| WO | WO-03064991 A2 | 8/2003 |
| WO | WO-2004048929 A2 | 6/2004 |
| WO | WO-2008156560 A1 | 12/2008 |
| WO | WO-2010151609 A1 | 12/2010 |
| WO | WO-2011081847 A1 | 7/2011 |
| WO | WO-2014201435 A1 | 12/2014 |

OTHER PUBLICATIONS

European search report with written opinion dated Nov. 27, 2017 for EP Application No. 15815993.

Ben-Oren, et al. Infrared nonlinear optical measurements of membrane potential in photoreceptor cells. Biophys J. Sep. 1996;71(3):1616-20.

Berkovic, et al. Interference between second-harmonic generation from a substrate and from an adsorbate layer. Journal of the Optical Society of America B-Optical Physics. 1989; 6:205-208.

Bethea. Experimental technique of dc induced SHG in liquids: measurement of the non linearity of CH2I2. Applied Optics. 1975; 14:1447-1451.

Bieri, et al. Micropatterned immobilization of a G protein-coupled receptor and direct detection of G protein activation. Nature Biotechnology. 1999; 17:1105-1108.

Bouevitch, et al. Probing membrane potential with nonlinear optics. Biophys J. Aug. 1993;65(2):672-9.

Boyd, et al. Local-field enhancement on rough surfaces with the use of optical 2nd-harmonic generation. Phys. Rev. B 1984; 30:519-526.

Campagnola, et al. High-resolution nonlinear optical imaging of live cells by second harmonic generation. Biophys J. Dec. 1999;77(6):3341-9.

Campagnola, et al. Second-harmonic imaging microscopy for visualizing biomolecular arrays in cells, tissues and organisms. Nat Biotechnol. Nov. 2003;21(11):1356-60.

Campagnola, et al. Three-dimensional high-resolution second-harmonic generation imaging of endogenous structural proteins in biological tissues. Biophysical Journal. 2002; 81:493-508.

Chen, et al. Detection of Molecular Monolayers by Optical Second-Harmonic Generation. Physical Review Letters. 1981; 46:1010-1012.

Clark, et al. Second harmonic generation properties of fluorescent polymer-encapsulated gold nanoparticles. J. Am. Chem. Soc. 2000; 122:10234-10235.

Clarke, et al. Conformational changes of fibrinogen after adsorption. Journal of Physical Chemistry B. 2005; 109:22027-22035.

Clays, et al. Nonlinear optical properties of proteins measured by hyper-rayleigh scattering in solution. Science. Nov. 26, 1993;262(5138):1419-22.

Cohen, et al. A Fluorescent Probe Designed for Studying Protein Conformational Change. PNAS. 2005; 102(4):965-970.

Conboy, et al. Studies of Alkane/water interfaces by total internal reflection second harmonic generation. J. Phys. Chem. 1994; 98:9688-9698.

Delprincipe et al. Two Photo and UV-Laser Flash Photlysis of CA Cage Dimethoynitrophenyl-EGTA-4. Cell Calcium. 1999; 25:85-91.

Ditcham, et al. An immunosensor with potential for the detection of viral antigens in body fluids, based on surface second harmonic generation. Biosens Bioelectron. May 2001;16(3):221-4.

Dworczak, et al. Electric field induced second harmonic generation (EFISH) experiments in the swivel cell: new aspects of an established method. Phys. Chem. Chem. Phys., 2000; 2:5057-5064.

Echo Qualified 1536—Well COC Source Microplate, Low Dead Volume (1536LDV) [online]. Labcyte. 2012.

Eisenthal. Photochemistry and photophysics of liquid interfaces by second harmonic spectroscopy. J. Phys. Chem. 1996; 100:12997-13006.

European search report dated Jan. 24, 2008 for EP Application No. 03736879.2.

European search report dated May 18, 2005 for EP Application No. 01995403.1.

European search report dated Dec.3, 2004 for EP Application No. 01957166.0.

(56) References Cited

OTHER PUBLICATIONS

Fejer, et al. Quasi-Phase-Matched Second Harmonic Generation Tuning and Tolerances. IEEE Journal of Quantum Electronics. 1992; 28(11):2631-2654.
Felderhof, et al. Optical second-harmonic generation from adsorbate layers in total-reflection geometry. Journal of the Optical Society of America B—Optical Physics. 1993; 10:1824-1833.
Feller, et al. Investigation of surface-induced alignment liquid-crystal molecules by optical second-harmonic generation. Physical Review A. 1991; 43(12), 6778-6792.
Finn, et al. Measurements of hyperpolarizabilities for some halogenated methanes. J. Chem. Phys. 1974; 60:454-458.
Fittinghoff. Collinear type II second-harmonic-generation frequency-resolved optical gating for use with high-numerical-aperature objectives, 1998, Opt Lett, 23(13), 1046-1048.
Galletto, et al. Enhancement of second harmonic response by adsorbates on gold colloids: the effect of aggregation. J. Phys. Chem. B. 1999; 103:8706-8710.
Ghanouni, et al. Agonist-induced conformational changes in the G-protein-coupling domain of the beta 2 adrenergic receptor. Proc Natl Acad Sci U S A. May 22, 2001;98(11):5997-6002. Epub May 15, 2001.
Ghanouni, et al. Functionally Different Agonists Induce Distinct Conformations in the G Protein Coupling Domain of the B2 Adrenergic Receptor. Journal of Biological Chemistry. 2001; 276:24433-24436.
Goh, et al. Absolute Orientation of Water-Molecules at the Neat Water-Surface. Journal of Physical Chemistry. 1988; 92:5074-5075.
Groves, et al. Micropatterning fluid bilayers on solid supports. Science. 1997; 275:651-653.
Harrick. Internal reflection spectroscopy. Harrick Scientific Corporation. 2nd printing 1979.
Heinz. Determination of molecular orientation of monlayer adsorbates by optical second-harmonic generation. Physical Review A. 1983; 28(3):1883-1885.
Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.
Huang, et al. Nonlinear optical properties of potential sensitive styryl dyes. Biophys J. May 1988;53(5):665-70.
Hubbard, et al. Nonlinear optical studies of a fluorinated poled polyimide guest-host system. Applied Physics Letters. 1994; 65(3):265-267.
International search report and written opinion dated Apr. 20, 2012 for PCT/US2012/030010.
International search report and written opinion dated Oct. 6, 2015 for PCT Application No. US-201538375.
International search report dated Jan. 22, 2002 for PCT/US2001/022411.
International search report dated Feb. 10, 2006 for PCT Application No. PCT/US2003/017807.
International search report dated Mar. 23, 2006 for PCT/US2002/022681.
International search report dated May 1, 2002 for PCT/US2001/046932.
International search report dated Oct. 20, 2001 for PCT/US2001/022412.
Jager, et al. Comparison of quasi-phase-matching geometries for second harmonic generation in poled polymer channel waveguides at 1.5 mm,. Appl. Phys. Lett.1996; 68:1183-1185.
Kajikawa, et al. Second harmonic generation in disperse-red-labeled poly(methyl methacrylate) Langmuir Blodgett film. Appl. Phys. Letters. May 3, 1993; 62(18):2161-2163.
Kemnitz, et al. The Phase of 2nd-Harmonic Light Generated at an Interface and Its Relation to Absolute Molecular-Orientation. Chemical Physics Letters. 1986; 131:285-290.
Khatchatouriants, et al. GFP is a selective non-linear optical sensor of electrophysiological processes in Caenorhabditis elegans. Biophys J. Nov. 2000;79(5):2345-52.
Kriech, et al. Using the intrinsic chirality of a molecule as a label-free probe to detect molecular adsorption to a surface by second harmonic generation. Applied Spectroscopy. 2005; 59:46-753.
Levine. Conjugated electron contributions to the second order hyperpolarizability of substituted benzene molecules J. Chem. Phys. 1975; 63:115-117.
Levine, et al. Absolute signs of hyperpolarizabilities in the liquid state. J. Chem. Phys. 1974; 60(10)3856-3858.
Levine, et al. Charge transfer complexes and hyperpolarizabilities. J. Chem. Phys. 1977; 66:1070-1074.
Levine, et al. Molecular hyperpolarizabilities determined from conjugated and nonconjugated organic liquids. Appl. Phys. Lett. 1974; 24:445-447.
Levine, et al. Second and third order hyperpolarizabilities of organic molecules. J. Chem. Phys. 1975; 63(6):2666-2682.
Levine, et al. Second Order Hyperpolarizability of a Polypeptide a-helix: Poly--y-benzyl-L-glutamate. J. Chem. Phys. 1976; 65(5):1989-1993.
Levine, et al. Ultraviolet dispersion of the donor-acceptor charge transfer contribution to the second order hyperpolarizability. J. Chem. Phys. 1978; 69(12): 5240-5245.
Lewis, et al. Second Harmonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.
MacBeath, et al. Printing Proteins as Microarrays for High-Throughput Function Determination. Science. 2000; 289:1760-1763.
McConnell, et al. Electronic and optical properties of chemically modified metal nanoparticles and molecularly bridged nanoparticle arrays. J. Phys. Chem. B. 2000; 104:8925-8930.
Millard, et al. Second harmonic imaging microscopy. Methods Enzymol. 2003;361:47-69.
Moreaux, et al. Membrane imaging by second harmonic generation microscopy. Journal of Optical Society of America B: Optical Physics. 2000; 17(10):1685-1694.
Moree, et al. Protein Conformational Changes Are Detected and Resolved Site Specifically by Second-Harmonic Generation. Biophys J. Aug. 18, 2015;109(4):806-15. doi: 10.1016/j.bpj.2015.07.016.
Notice of Allowance dated May 6, 2013 for U.S. Appl. No. 12/571,342, filed Sep. 30, 2009, 9 pages.
Office action dated Jan. 30, 2015 for U.S. Appl. No. 13/834,521.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 14, 2015 for U.S. Appl. No. 13/834,809.
Office action dated Apr. 21, 2004 for U.S. Appl. No. 09/907,038.
Office action dated Apr. 21, 2015 for U.S. Appl. No. 13/838,340.
Office action dated Apr. 21, 2015 for U.S. Appl. No. 13/838,491.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 15, 2015 for U.S. Appl. No. 13/834,521.
Office action dated Sep. 20, 2005 for U.S. Appl. No. 10/467,098.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Oral Abstracts from the Society of Biomolecular Sciences 14th Annual Conference and Exhibition: St. Louis, Missouri Apr. 6-10, 2008. J. Biomol Screen 2008 13: 697. DOI: 10.1177/1087057108322219.
Oudar, et al. Hyperpolarizabilities of the nitroanilines and their relations to the excited state dipole moment. J. Chem. Phys. 1977; 66. 2664-2668.

(56) References Cited

OTHER PUBLICATIONS

Oudar, et al. Optical nonlinearities of conjugated molecules. Stilbene derivatives and highly polar aromatic compounds. J. Chem. Phys. 1977; 67(2):446-457.

Paige, et al. Estrogen receptor (ER) modulators each induce distinct conformational changes in ER alpha and ER beta. Proc Natl Acad Sci U S A. Mar. 30, 1999;96(7):3999-4004.

Paszti, et al. Sum frequency generation vibrational spectroscopy studies of protein adsorption on oxide-covered Ti surfaces. Journal of Physical Chemistry B. 2004; 108:7779-7787.

Peleg, et al. Nonlinear optical measurement of membrane potential around single molecules at selected cellular sites. Proc Natl Acad Sci U S A. Jun. 8, 1999;96(12):6700-4.

Pitchford, et al. Direct, real-time detection of kinae type II inhibitors using second harmonic generation (SHG) detection. 2011. Poster T380. Retrieved Apr. 18, 2012. www.labautopedia.com/mw/images/T380posterSBS2011.jpg.

Polizzi, et al. (2004). Ellipsometric approach for the real-time detection of label-free protein absroption by second harmonic generation. Journal of the American Chemical Society. 2004; 126:5001-5007.

Reider, et al. Second-order Nonlinear Optical Effects at Surfaces and Interfaces: recent advances. In Electromagnetic Waves: Recent Developments in Research, vol. 2, Photonic Probes of Surfaces. Halevia, P., editor. Elsevier Science, Amsterdam. Chapter 9. 1995. 415-478.

Request for Continued Examination filed on Jan. 13, 2009 for U.S. Appl. No. 11/327,199, filed Jan. 5, 2006, 6 pages.

Request for Continued Examination filed on Jul. 16, 2012 for U.S. Appl. No. 12/571,342, filed Sep. 30, 2009, 10 pages.

Response to Non-Final Office Action filed on Apr. 1, 2013 for U.S. Appl. No. 12/571,342, filed Sep. 30, 2009, 9 pages.

Response to Non-Final Office Action filed on Aug. 18, 2011 for U.S. Appl. No. 12/571,342, filed Sep. 30, 2009, 6 pages.

Response to Non-Final Office Action filed on Dec. 14, 2007 for U.S. Appl. No. 11/327,199, filed Jan. 5, 2006, 8 pages.

Rinuy, et al. Second harmonic generation of glucose oxidase at the air/water interface. Biophysial Journal. 1999; 77:3350-3355.

Salafsky. Detection of protein conformational change by optical second-harmonic generation. J Chem Phys. Aug. 21, 2006;125(7):074701.

Salafsky, et al. A second-harmonic-active unnatural amino acid as a structural probe of biomolecules on surfaces. J. Phys. Chem. B, 2008, 112 (47), pp. 15103-15107.

Salafsky, et al. Protein absorption at interfaces detected by second-harmonic generation.J. Phys. Chem. B. 2004; 108(10):3376. Additions and Corrections.

Salafsky, et al. Protein absorption at interfaces detected by second-harmonic generation.Journal of Physical Chemistry B. 2000; 104:7752-7755.

Salafsky, et al. Second Harmonic Spectroscopy: Detection and Orientation of Molecules at a Biomembrane Interface. Chemical Physics Letters 2000; 319:435-439.

Salafsky, et al. SHG labels for detection of molecules by second harmonic generation. Chemical Physics Letters. 2001; 342:485-491.

Salafsky, J. (Apr. 2008). "Second-Harmonic Generation (SHG) for Identification of Allosteric D & Conformation-Specific Compounds" PowerPoint Presentation presented to SBS, 30 pages.

Salafsky, J. (Apr. 15, 2009). "Detection Method for Conformational Change Second-Harmonic Generation Provides a Molecular-Level, Functional Readout in Real Time" Gen Eng & Biotech News, 2 pages.

Salafsky. Second-harmonic generation as a probe of conformational change in molecules. Chemical Physics Letters. 2003; 381(5):705-709.

Salafsky. Second-harmonic generation for studying structural motion of biological molecules in real time and space. Phys Chem Chem Phys. Nov. 14, 2007;9(42):5704-11. Epub Sep. 7, 2007.

Samanta, et al. Excited state dipole moment of PRODAN as determined from transient dieletric loss measurements. Journal of Physical Chemistry A. 2000; 104:8972-8975.

Seok, et al. Topology of allosteric regulation of lactose permease. Proc Natl Acad Sci U S A. Dec. 9, 1997;94(25):13515-9.

Shen. Optical Second Harmonic Generation at Interfaces. Annual Review of Physical Chemistry. 1989; 40(1):327-350.

Shen.. Surface properties probed by second-harmonic and sum-frequency generation. Nature. 1989; 337: 20 519-525.

Shen. The Principles of Nonlinear Optics, John Wiley & Sons, New York. 1984.

Singer, et al. Measurements of molecular second-order optical susceptibilities using dc-induced second harmonic generation. J. Chem. Phys. 1981; 75:3572-3580.

Summerer, et al. A genetically encoded fluorescent amino acid. Proc Natl Acad Sci U S A. Jun. 27, 2006;103(26):9785-9. Epub Jun. 19, 2006.

Theodossiou, et al. Thermally Induced Irreversible Conformational Changes in Collagen Probed by Optical Second Harmonic Generation and Laser-induced Fluorescence, 2002; 17:34-41.

Thermo Scientific Matrix Microplate Data Sheet [online]. Thermo Scientific. 2008.

Wang, et al. In situ, nonlinear optical probe of Surfactant Adsorption on the Surface of Microparticles in Colloids. Langmuir 2000, 16, 2475-2481.

Wang, et al. Polarity of liquid interfaces by second harmonic generation spectroscopy, 1997, J Phys Chem A, 101, 713-718.

Weidner, et al. Sum frequency generation and solid-state NMR study of the structure, orientation, and dynamics of polystyrene-adsorbed peptides. Proc Natl Acad Sci U S A. Jul. 27, 2010;107(30):13288-93. doi: 10.1073/pnas.1003832107. Epub Jul. 13, 2010.

Yang, et al. Surface second harmonic generation (SSHG)—a new scheme for immunoassay. Proceedings of the SPIE. 1996; 2676:290-296. http://dx.doi.org/10.1117/12.238808.

EP15815993.9 Office Action dated Jul. 2, 2019.

JP2016-575913 Office Action dated May 27, 2019 (w/ English translation).

FIG. 1A Fluorescence

FIG. 1B SHG

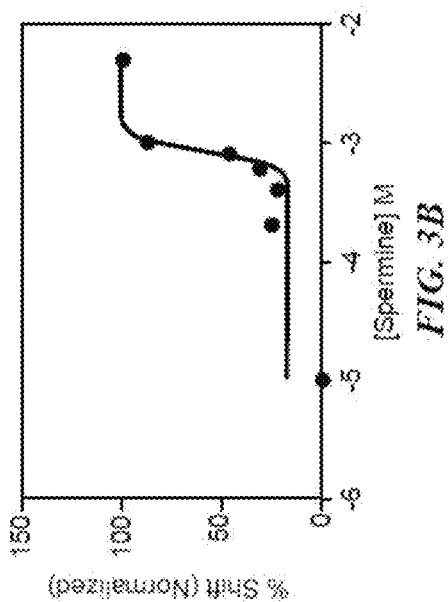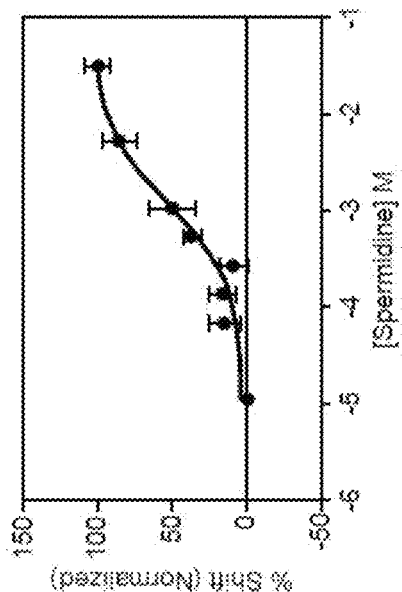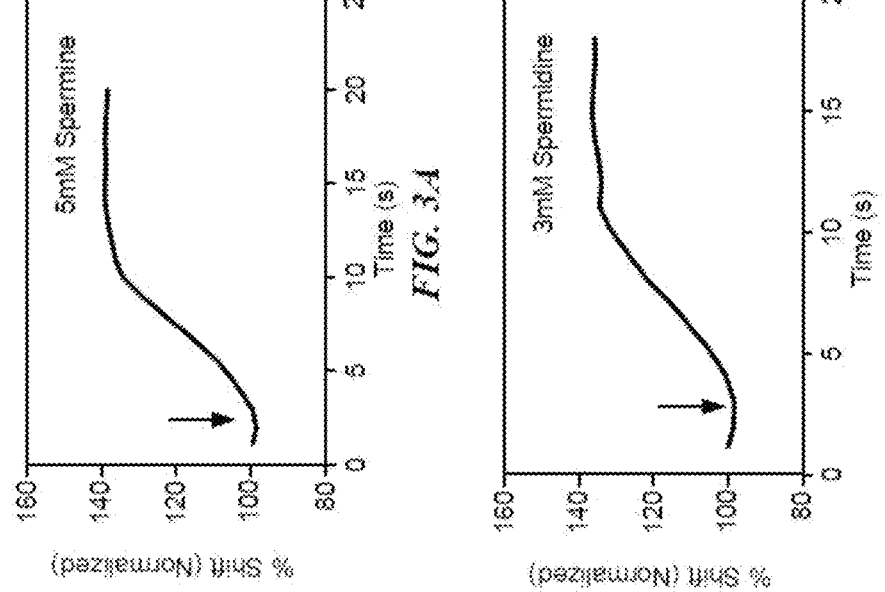

FIG. 16B
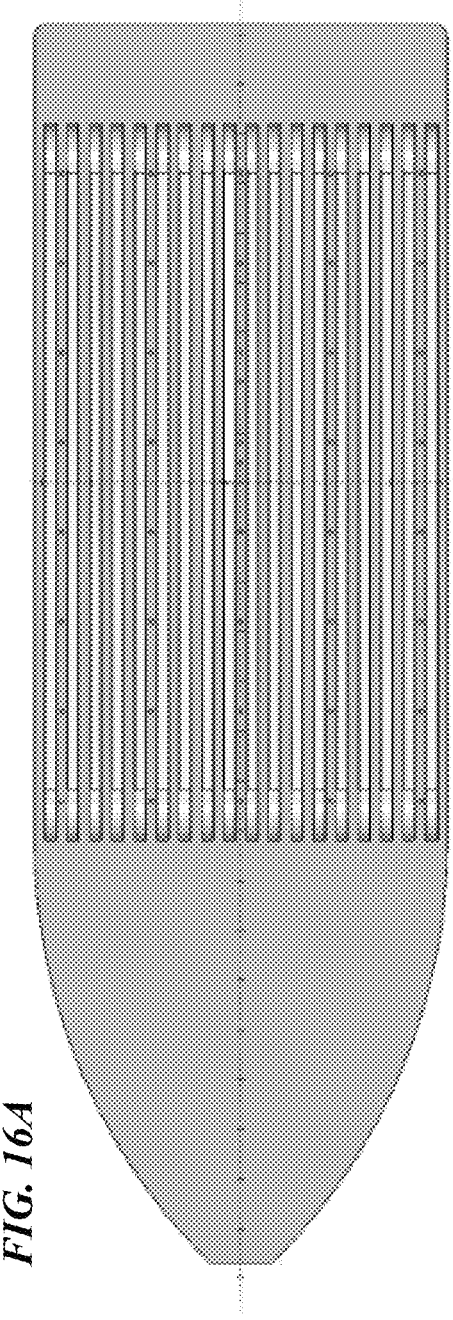
FIG. 16C
FIG. 16A

SYSTEMS AND METHODS FOR HIGH THROUGHPUT ANALYSIS OF CONFORMATION IN BIOLOGICAL ENTITIES

CROSS-REFERENCE

This application is a Continuation Application of U.S. application Ser. No. 14/754,465, filed Jun. 29, 2015, which claims the benefit of U.S. Provisional Application No. 62/019,285, filed Jun. 30, 2014, each of which is incorporated herein by reference.

STATEMENT AS TO FEDERALLY SPONSORED RESEARCH

This invention was made with the support of the United States government under Grant Number IIP-1256619 from the National Science Foundation.

BACKGROUND OF THE INVENTION

Over the past two decades, the advent of high throughput experimentation has transformed the way life science and biomedical research is carried out. A convergence of technologies in fields such as genetic engineering, organic chemistry, materials science, microfabrication and microelectronics has led to new technology platforms (e.g. microarray technologies, microfluidic devices and systems, bead-based combinatorial compound libraries and assay systems, and microplate-based assay systems) to address applications ranging from high throughput screening of compound libraries for drug discovery to rapid whole genome sequencing.

Examples of high throughput screening systems for drug discovery include microfluidics-based platform technologies for running continuous-flow assays (e.g. receptor-ligand binding assays and cell-based assays for identifying receptor agonists), and microplate-based systems in which binding reactions, enzymatic reactions, or cell-based assays are run in a microwell plate format, and automated liquid-dispensing stations and plate-handling robotics provide for automated sample preparation, assay, and detection steps. The majority of existing high throughput platform technologies for drug discovery utilize fluorescence-based optical detection. Although fluorescence techniques provide for very high detection sensitivity, and are generally much more environmentally friendly than the more traditional, radioisotope-based approaches that predominated in biological assay methodologies of two decades ago, there are a number of drawbacks to the use of fluorescence. Examples include: (i) the requirement for sophisticated light sources, detectors, and optical systems, the performance of which are often sensitive to misalignment or instrumental drift, and (ii) photo-bleaching phenomena, which may result in degradation of signal over time in samples subjected to repeat measurements.

Another, more serious limitation of existing high throughput screening technologies stems from the growing awareness that a number of potential therapeutic targets, e.g. potential cancer therapeutic targets, that are attractive targets from a biological perspective are intractable ("undruggable") from a chemical standpoint because they are generally not amenable to conventional drug discovery approaches. These protein targets typically possess a relatively large contact area when interacting with other proteins (i.e. through protein-protein interactions) or due to the fact that they possess a ligand that binds with extremely high affinity to the active site of the protein. In either case, finding a conventional small molecule or biologic (protein) drug candidate that will block the interaction (i.e. interfere with and/or obscure the large contact area in the case of protein-protein interactions, or displace the high affinity ligand) is extremely difficult. Allosteric modulators for such "undruggable" targets offer an attractive therapeutic solution. By definition, allosteric molecules bind to a site other than a protein's active site, thereby changing the protein's conformation with a concomitant functional effect (e.g. activation of a receptor). Allosteric modulation of target proteins has the added benefit of not having to rely on inhibition or competition with the binding of the natural ligand to the protein, which can result in unintended clinical side effects. However, it has been difficult to identify allosteric modulators using currently available conventional techniques. For example, structural information obtained from X-ray crystallography or NMR methods is often of limited value for drug discovery purposes due to low throughput, low sensitivity, the non-physiological conditions utilized, the size of the protein amenable to the technique, and many other factors. What is needed, therefore are high throughput techniques for screening collections of candidate compounds to rapidly identify agents capable of, for example, allosteric modulation of the target protein's conformation.

As described more fully below, second harmonic generation (SHG) is a nonlinear optical process which may be configured as surface-selective detection technique that enables detection of conformational change in proteins and other biological targets (as described previously, for example, in U.S. Pat. No. 6,953,694, and U.S. patent application Ser. No. 13/838,491). In order to deploy SHG-based detection of conformational change in a high throughput format, it may be advantageous to design novel mechanisms for rapid, precise, and interchangeable positioning of substrates (comprising the biological targets to be analyzed) with respect to the optical system used to deliver excitation light, which at the same time ensure that efficient optical coupling between the excitation light and the substrate surface is maintained. One preferred format for high throughput optical interrogation of biological samples is the glass-bottomed microwell plate.

The systems and methods disclosed herein provide mechanisms for coupling the high intensity excitation light required for SHG and other nonlinear optical techniques to a substrate, e.g. the glass substrate in a glass-bottomed microwell plate, by means of total internal reflection in a manner that is compatible with the requirements for a high throughput analysis system.

SUMMARY OF THE INVENTION

Disclosed herein are methods for determining interactions between biological entities and test entities, comprising: (a) contacting each of at least four biological entities with at least one test entity; (b) illuminating each of the at least four biological entities with one or more excitation light beams using a surface selective optical technique; and (c) determining whether or not a conformational change was induced in each of the at least four biological entities through contact with the at least one test entity; wherein determinations of conformational change are performed at an average rate of at least 10 test entities tested per hour. In some embodiments, the determinations of conformational change are performed at an average rate of at least 100 test entities tested per hour.

In some embodiments, the at least four biological entities are the same. In some embodiments, the at least four biological entities are different. In some embodiments, the biological entities are selected from the group consisting of cells, proteins, peptides, receptors, enzymes, antibodies, DNA, RNA, oligonucleotides, small molecules, and carbohydrates, or any combination thereof. In some embodiments, the biological entities are drug targets or portions thereof.

In some embodiments, each of the at least four biological entities are situated in a different discrete region on a substrate. In some embodiments, each discrete region comprises an area of up to about 100 $mm^2$ on a substrate surface. In some embodiments, each discrete region comprises a supported lipid bilayer. In some embodiments, the biological entities are tethered to or embedded within the supported lipid bilayer.

In some embodiments, the at least one test entity is selected from the group consisting of cells, proteins, peptides, receptors, enzymes, antibodies, DNA, RNA, oligonucleotides, small molecules, and carbohydrates, or any combination thereof. In some embodiments, the test entity is a drug candidate or portion thereof.

In some embodiments, the contacting step occurs in solution and comprises utilizing a pre-programmed fluid dispensing unit to dispense the at least one test entity. In some embodiments, the contacting step comprises contacting each of the at least four biological entities with a different test entity. In some embodiments, the contacting step comprises serially contacting each of the at least four biological entities with at least 100 different test entities. In some embodiments, the contacting step comprises serially contacting each of the at least four biological entities with at least 10,000 different test entities.

In some embodiments, the one or more excitation light beams are provided by one or more lasers. In some embodiments, the surface selective optical detection technique comprises the use of total internal reflection of at least one excitation light beam from a planar substrate surface.

In some embodiments, the determining step further comprises analyzing a non-linear optical signal. In some embodiments, the non-linear optical signal is selected from the group consisting of second harmonic light, sum frequency light, and difference frequency light.

In some embodiments, the methods further comprise moving said substrate relative to the position of one or more external sources of the one or more excitation light beams. In some embodiments, each discrete region is optically coupled with an entrance prism and a different exit prism that are both integrated with a bottom surface of the substrate. In some embodiments, the illuminating step comprises directing incident excitation light onto an entrance prism positioned adjacent to, but not directly below, each of the discrete regions. In some embodiments, the methods further comprise collecting non-linear optical signals generated at each of the discrete regions upon illumination using an exit prism positioned adjacent to, but not directly below, each of the discrete regions, and directing said non-linear optical signals to a detector. In some embodiments, the methods further comprise repeating the illuminating and determining steps a plurality of times after said contacting step, thereby determining conformational changes in each of the at least four biological entities as a function of time.

Also disclosed herein are devices comprising: (a) a substrate, the substrate comprising: (i) an M×N array of discrete regions formed on a surface of the substrate, wherein M is the number of rows of discrete regions and N is the number of columns of discrete regions in the array, and each discrete region is configured for containing a biological entity, and (ii) an R×S array of prisms integrated with the substrate and optically coupled to the discrete regions, wherein R is the number of rows of prisms and S is the number of columns of prisms in the array; wherein R=M+2 and S=N, or R=M and S=N+2.

In some embodiments, each of the discrete regions is optically coupled with at least one input prism and at least one output prism, and wherein the input prism and the output prism are spatially distinct. In some embodiments, M=8 and N=12. In some embodiments, M=16 and N=24. In some embodiments, M=32 and N=48. In some embodiments, M is greater than 4 and N is greater than 4. In some embodiments, each discrete region comprises a supported lipid bilayer or is configured to facilitate the formation of a supported lipid bilayer. In some embodiments, the devices further comprise a well-forming component bonded to a top surface of the substrate in order to isolate each discrete region in a separate well. In some embodiments, each of the discrete regions comprises an area of up to about 100 $mm^2$. In some embodiments, each discrete region or well is located directly above a single prism of the array of prisms integrated with the substrate. In some embodiments, the substrate is composed of glass, fused-silica, or plastic.

Disclosed herein are injection molding processes for fabricating a prism array part from a plastic, the process comprising the use of two or more mold ejection devices to apply uniform pressure to the prism array part during a mold release step.

In some embodiments, the plastic is selected from the group consisting of cyclic olefin copolymer (COC), cyclic olefin polymer (COP), and acrylic. In some embodiments, the two or more mold ejection devices impact the prism array part only in regions where the optical performance of the part is non-critical. In some embodiments, the two or more mold ejection devices comprise an array of m×n blade-like ejector features. In some embodiments, m is greater than 2 and less than 20. In some embodiments, n is greater than 2 and less than 20.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-D show data that demonstrate the detection of spermine- or spermidine-induced conformational changes in alpha-synuclein using second harmonic light generation. FIG. 3A shows the SHG response in real time upon exposure of alpha-synuclein to 5 mM spermine. The arrow denotes spermine addition. The change in SHG intensity is normalized to the value just prior to injection. FIG. 3B shows the dose response curve (plotted on a log scale) for spermine-induced conformational change in alpha-synuclein as measured by SHG (the change in SHG concentration is quantified as percent shift). FIG. 3C shows the SHG response in real time upon exposure of alpha-synuclein to 3 mM spermidine. The arrow denotes spermidine addition. The change in SHG intensity is normalized to the value just prior to injection. FIG. 3D shows the dose response curve (plotted on a log scale) for spermidine-induced conformational change in alpha-synuclein as measured by SHG (the change in SHG concentration is quantified as percent shift). Error bars=SEM. N=3.

FIG. 8A: top-front axonometric view. FIG. 8B: top-rear axonometric view. FIG. 8C: bottom-front axonometric view.

FIG. 10A: top axonometric view. FIG. 10B: bottom axonometric view.

FIG. 10C: top axonometric view. FIG. 10D: bottom axonometric view.

FIG. 13A: top view. FIG. 13B: front view. FIG. 13C: right side view.

FIGS. 16A-C show an example of an improved prism array design according to the present disclosure. FIG. 16A: top view. FIG. 16B: front view. FIG. 16C: right side view.

DETAILED DESCRIPTION OF THE INVENTION

The systems and methods disclosed herein relate to high throughput analysis of conformation in biological entities. In addition, the systems and methods described are equally suitable for high throughput analysis of orientation or conformational change. In some aspects of the present disclosure, systems and methods are described for determining orientation, conformation, or changes in orientation or conformation of biological entities in response to contacting the biological entities with one or more test entities. As used herein, determining orientation, conformation, or changes thereof may involve measurement of a nonlinear optical signal which is related to and/or proportional to the average orientation of a nonlinear-active label or tag. As used herein, "high throughput" refers to the ability to perform rapid analysis of conformation for a large plurality of biological entities optionally contacted with one or more test entities, or to the ability to perform rapid analysis of conformation for one or more biological entities optionally contacted with a large plurality of test entities, or to any combination of these two modalities. In general, the systems and methods disclosed rely on the use of second harmonic generation (SHG) or related nonlinear optical techniques for detection of orientation, conformation, or conformational change, as described previously, for example, in U.S. Pat. No. 6,953,694, and U.S. patent application Ser. No. 13/838,491.

Detection of Conformation Using Second Harmonic Generation

Figure 1:
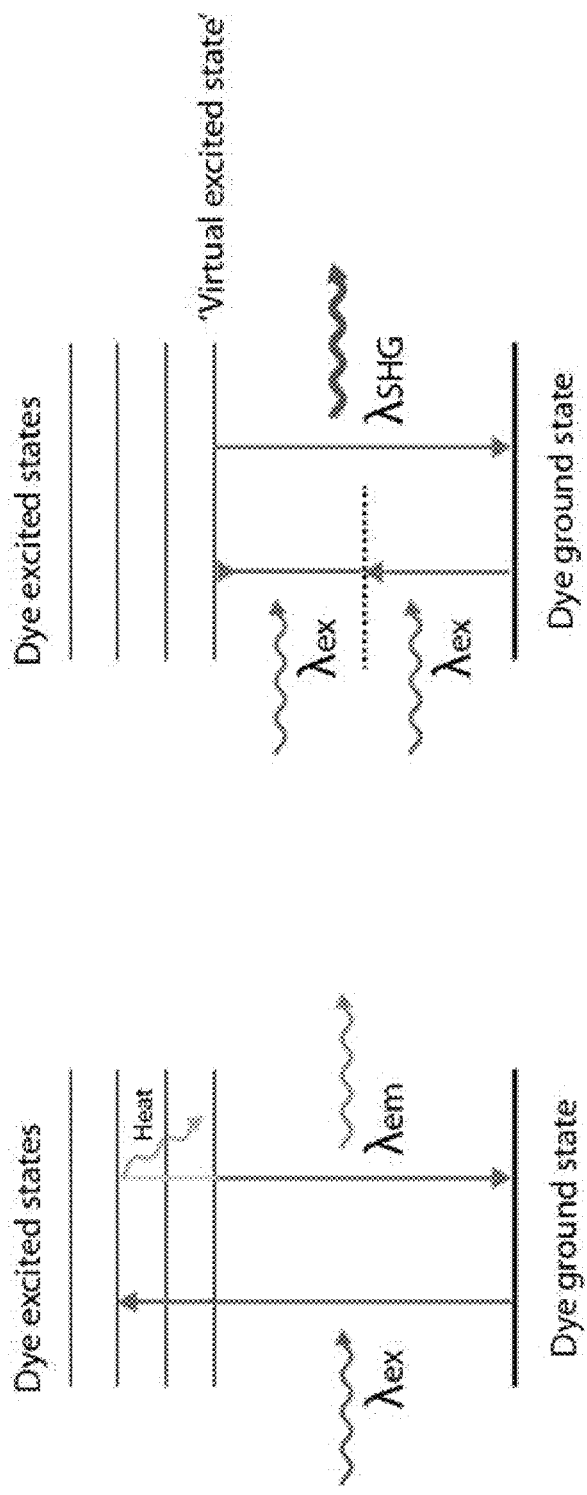
FIG. 1A provides a schematic illustration of the energy level diagrams for fluorescence (an absorption process).
FIG. 1B provides a schematic illustration of the energy level diagrams for second harmonic generation (a two photon scattering process).

Second harmonic generation, in contrast to the more widely used fluorescence-based techniques, is a nonlinear optical process, in which two photons of the same excitation wavelength or frequency interact with a nonlinear material and are re-emitted as a single photon having twice the energy, i.e. twice the frequency and half the wavelength, of the excitation photons (FIG. 1). Second harmonic generation only occurs in nonlinear materials lacking inversion symmetry (i.e. in non-centrosymmetric materials), and requires a high intensity excitation light source. It is a special case of sum frequency generation, and is related to other nonlinear optical phenomena such as difference frequency generation.

Second harmonic generation and other nonlinear optical techniques can be configured as surface-selective detection techniques because of their dependence on the orientation of the nonlinear-active species. Tethering of the nonlinear-active species to a surface, for example, can instill an overall degree of orientation that is absent when molecules are free to undergo rotational diffusion in solution. An equation commonly used to model the orientation-dependence of nonlinear-active species at an interface is:

$$\chi^{(2)} = N_s \langle \alpha^{(2)} \rangle$$

where $\chi^{(2)}$ is the nonlinear susceptibility, $N_s$ is the total number of nonlinear-active molecules per unit area at the interface, and $\langle \alpha^{(2)} \rangle$ is the average orientation of the nonlinear hyperpolarizability ($\alpha^{(2)}$) of these molecules. The intensity of SHG is proportional to the square of the nonlinear susceptibility, and is thus dependent on both the number of oriented nonlinear-active species at the interface and to changes in their average orientation.

Second harmonic generation and other nonlinear optical techniques may be rendered additionally surface selective through the use of total internal reflection as the mode for delivery of the excitation light to the optical interface on which nonlinear-active species have been immobilized. Total internal reflection of the incident excitation light creates an "evanescent wave" at the interface, which may be used to selectively excite only nonlinear-active labels that are in close proximity to the surface, i.e. within the spatial decay distance of the evanescent wave, which is typically on the order of tens of nanometers. Total internal reflection may also be used to excite fluorescence in a surface-selective manner, for example to excite a fluorescence donor attached to the optical interface, which then transfers energy to a suitable acceptor molecule via a fluorescence resonance energy transfer (FRET) mechanism. In the present disclosure, the evanescent wave generated by means of total internal reflection of the excitation light is preferentially used to excite a nonlinear-active label or molecule. The efficiency of exciting nonlinear active species will depend strongly on both their average orientation and on their proximity to the interface.

Figure 2:
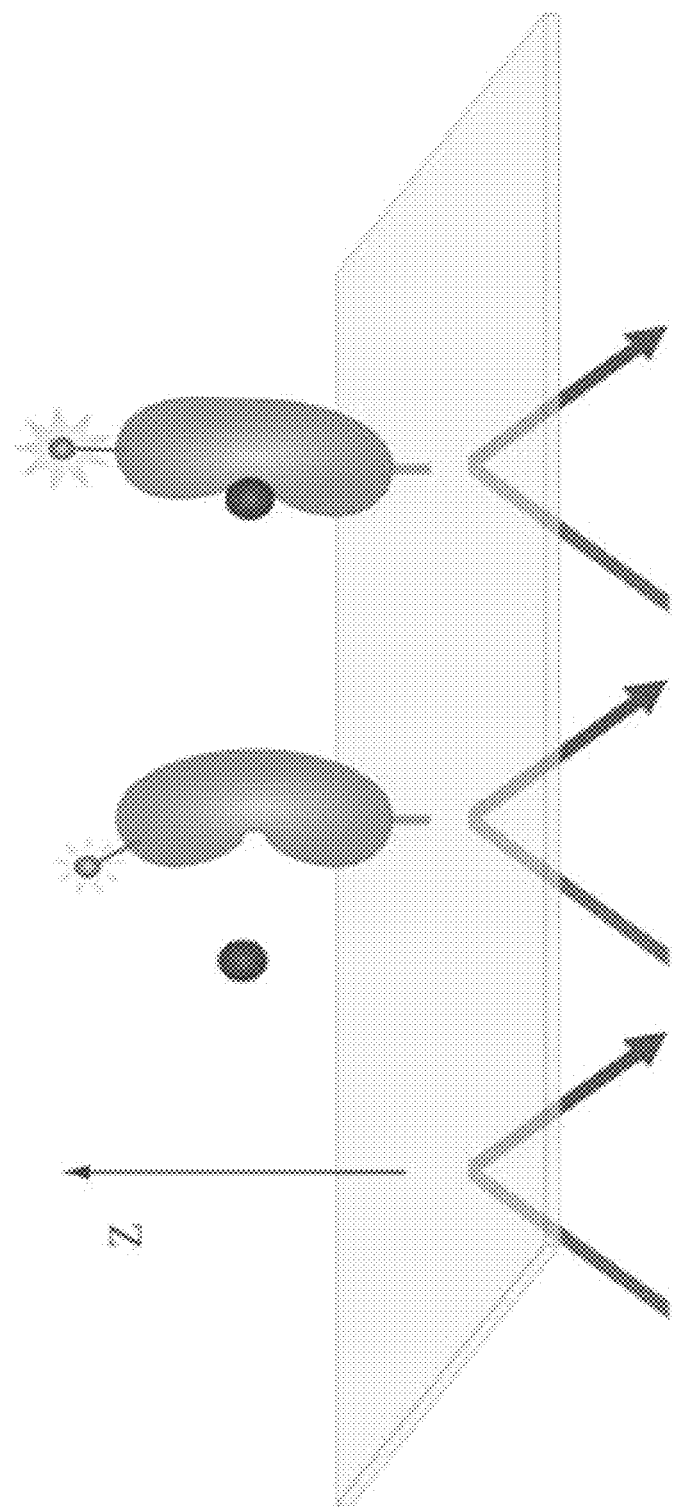
FIG. 2 provides a schematic illustration of a conformational change in a protein (labeled with a nonlinear-active tag) which is induced by binding of a ligand, and its impact on the distance and/or orientation of a nonlinear-active label relative to an optical interface to which the protein is attached.

This surface selective property of SHG and other nonlinear optical techniques can be exploited to detect conformational change in biological molecules immobilized at interfaces. For example, conformational change in a receptor molecule due to binding of a ligand, might be detected using a nonlinear-active label or moiety wherein the label is attached to or associated with the receptor such that the conformational change leads to a change in the orientation or distance of the label with respect to the interface (FIG. 2), and thus to a change in a physical property of the nonlinear optical signal. Until recently, the use of surface-selective nonlinear optical techniques has been confined mainly to applications in physics and chemistry, since relatively few biological samples are intrinsically non-linearly active. Recently, the use of second harmonic active labels ("SHG labels") has been introduced, allowing virtually any molecule or particle to be rendered highly non-linear active. The first example of this was demonstrated by labeling the protein cytochrome c with an oxazole dye and detecting the protein conjugate at an air-water interface with second harmonic generation [Salafsky, J., "'SHG-labels' for Detection of Molecules by Second Harmonic Generation", Chem. Phys. Lett. 342(5-6):485-491 (2001)]. Examples of SHG data that demonstrate the detection of spermine- or spermidine-induced conformational changes in alpha-synuclein are shown in FIG. 3.

Surface-selective nonlinear optical techniques are also coherent techniques, meaning that the fundamental and nonlinear optical light beams have wave fronts that propagate through space with well-defined spatial and phase relationships. The use of surface-selective nonlinear optical detection techniques for analysis of conformation of biological molecules or other biological entities has a number of inherent advantages over other optical approaches, including: i) sensitive and direct dependence of the nonlinear signal on the orientation and/or dipole moment(s) of the nonlinear-active species, thereby conferring sensitivity to conformational change; (ii) higher signal-to-noise (lower background) than fluorescence-based detection since the nonlinear optical signal is generated only at surfaces that create a non-centrosymmetric system, i.e. the technique inherently has a very narrow "depth-of-field"; (iii) as a result of the narrow "depth of field", the technique is useful when measurements must be performed in the presence of a overlaying solution, e.g. where a binding process might be obviated or disturbed by a separation or rinse step. This aspect of the technique may be particularly useful for performing equilibrium binding measurements, which require the presence of bulk species, or kinetics measurements where the measurements are made over a defined period of time; (iv) the technique exhibits lower photobleaching and heating effects than those that occur in fluorescence, due to the facts that the two-photon absorption cross-section is typically much lower than the one-photon absorption cross-section for a given molecule, and that SHG (and sum frequency generation or difference frequency generation) involves scattering, not absorption; (v) minimal collection optics are required and higher signal to noise is expected since the fundamental and nonlinear optical beams (e.g., second harmonic light) have well-defined incoming and outgoing directions with respect to the interface. This is particularly advantageous compared to fluorescence-based detection, as fluorescence emission is isotropic and there may also be a large fluorescence background component to detected signals arising from out-of-focal plane fluorescent species.

High Throughput Systems and Methods

Systems and methods are disclosed herein for implementing high throughput analysis of conformation in biological entities based on the use of second harmonic generation or related nonlinear optical detection techniques. As used herein, "high throughput" is a relative term used in comparison to structural measurements performed using traditional techniques such as NMR or X-ray crystallography. As will be described in more detail below, the SHG-based methods and systems disclosed herein are capable of performing structural determinations at a rate that is at least an order-of-magnitude faster than these conventional techniques.

In one aspect, this disclosure provides a method for high throughput detection of conformation or conformational change in one or more biological entities, the method comprising (i) labeling one or more target biological entities, e.g. protein molecules, with a nonlinear-active label or tag, (ii) immobilizing the one or more labeled target biological entities at one or more discrete regions of a planar substrate surface, wherein the substrate surface further comprises an optical interface, (iii) sequentially exposing each discrete region to excitation light by changing the position of the substrate relative to an external light source, (iv) collecting a nonlinear optical signal emitted from each discrete region as it is exposed to excitation light, and (v) processing said nonlinear optical signal to determine an orientation, conformation, or conformational change of each of the one or more biological entities. In another aspect, the method further comprises (vi) contacting each of the one or more biological entities with one or more test entities following the first exposure to excitation light, (vii) subsequently re-exposing each discrete region to excitation light one or more times, (viii) collecting a nonlinear optical signal from each discrete region as it is exposed to excitation light, and (ix) processing said nonlinear optical signals to determine whether or not a change in orientation or conformation has occurred in the one or more biological entities as a result of contacting with said one or more test entities. In one aspect of the method, nonlinear optical signals are detected only once following contact of the one or more biological entities with one or more test entities (i.e. endpoint assay mode), and then used to determine whether or not conformational change has occurred. In another aspect, nonlinear optical signals are collected repeatedly and at defined time intervals following contact of the one of more biological entities with one or more test entities (i.e. kinetics mode), and then used to determine the kinetics of conformational change in the one or more biological entities. In a preferred aspect of the method, each discrete region of the substrate comprises a supported lipid bilayer structure, and biological entities are immobilized in each discrete region by means of tethering to or embedding in the lipid bilayer. In another preferred aspect of the method, the excitation light is delivered to the substrate surface, i.e. the optical interface, by means of total internal reflection, and the nonlinear optical signals emitted from the discrete regions of the substrate surface are collected along the same optical axis as the reflected excitation light.

In order to implement high throughput analysis of conformation or conformational change using nonlinear optical detection, the systems described herein require several components (illustrated schematically in FIG. 4), including (i) at least one suitable excitation light source and optics for delivering the at least one excitation light beam to an optical interface, (ii) an interchangeable substrate comprising the optical interface, to which one or more biological entities have been tethered or immobilized in discrete regions of the substrate, (iii) a high-precision translation stage for positioning the substrate relative to the at least one excitation light source, and (iv) optics for collecting nonlinear optical signals generated as a result of illuminating each of the discrete regions of the substrate with excitation light and delivering said nonlinear signals to a detector, and (v) a processor for analyzing the nonlinear optical signal data received from the detector and determining conformation or conformational change for the one or more biological entities immobilized on the substrate. In some aspects, the systems and methods disclosed herein further comprise the use of (vi) a programmable fluid-dispensing system for delivering test entities to each of the discrete regions of the substrate, and (vii) the use of plate-handling robotics for automated positioning and replacement of substrates at the interface with the optical system.

The methods and systems disclosed herein may be configured for analysis of a single biological entity contacted with a plurality of test entities, or for analysis of a plurality of biological entities contacted with a single test entity, or any combination thereof. When contacting one or more biological entities with a plurality of test entities, the contacting step may be performed sequentially, i.e. by exposing the immobilized biological entity to a single test entity for a specified period of time, followed by an optional rinse step to remove the test entity solution and regenerate the immobilized biological entity prior to introducing to the next test entity, or the contacting step may be performed in parallel, i.e. by having a plurality of discrete regions comprising the same immobilized biological entity, and exposing the biological entity in each of the plurality of discrete regions to a different test entity. The methods and systems disclosed herein may be configured to perform analysis of conformational change in at least one biological entity, at least two biological entities, at least four biological entities, at least six biological entities, at least eight biological entities, at least ten biological entities, at least fifteen biological entities, or at least twenty biological entities. In some aspects, methods and systems disclosed herein may be configured to perform analysis of conformational change in at most twenty biological entities, at most fifteen biological entities, at most ten biological entities, at most eight biological entities, at most six biological entities, at most four biological entities, at most two biological entities, or at most one biological entity. Similarly, the methods and systems disclosed herein may be configured to perform analysis of conformational change upon exposure of the one or more biological entities to at least 1 test entity, at least 5 test entities, at least 10 test entities, at least 50 test entities, at least 100 test entities, at least 500 test entities, at least 1,000 test entities, at least 5,000 test entities, at least 10,000 test entities, or at least 100,000 test entities. In some aspects, the methods and systems disclosed herein may be configured to perform analysis of conformational change upon exposure of the one or more biological test entities to at most 100,000 test entities, at most 10,000 test entities, at most 5,000 test entities, at most 1,000 test entities, at most 500 test entities, at most 100 test entities, at most 50 test entities, at most 10 test entities, at most 5 test entities, or at most 1 test entity.

Biological Entities and Test Entities

As used herein, the phrase "biological entities" comprises but is not limited to cells, proteins, peptides, receptors, enzymes, antibodies, DNA, RNA, biological molecules, oligonucleotides, solvents, small molecules, synthetic molecules, carbohydrates, or any combination thereof. Similarly, the phrase "test entities" also comprises but is not limited to cells, proteins, peptides, receptors, enzymes, antibodies, DNA, RNA, biological molecules, oligonucleotides, solvents, small molecules, synthetic molecules, carbohydrates, or any combination thereof. In some aspects, biological entities may comprise drug targets, or portions thereof, while test entities may comprise drug candidates, or portions thereof.

Nonlinear-Active Labels and Labeling Techniques

As noted above, most biological molecules are not intrinsically nonlinear-active. Exceptions include collagen, a structural protein that is found in most structural or load-bearing tissues. SHG microscopy has been used extensively in studies of collagen-containing structures, for example, the cornea. Other biological molecules or entities must be rendered nonlinear-active by means of introducing a nonlinear-active moiety such as a tag or label. A label for use in the present invention refers to a nonlinear-active moiety, tag, molecule, or particle which can be bound, either covalently or non-covalently to a molecule, particle or phase (e.g., a lipid bilayer) in order to render the resulting system more nonlinear optical active. Labels can be employed in the case where the molecule, particle or phase (e.g., lipid bilayer) is not nonlinear active to render the system nonlinear-active, or with a system that is already nonlinear-active to add an extra characterization parameter into the system. Exogenous labels can be pre-attached to the molecules, particles, or other biological entities, and any unbound or unreacted labels separated from the labeled entities before use in the methods described herein. In a specific aspect of the methods disclosed herein, the nonlinear-active moiety is attached to the target molecule or biological entity in vitro prior to immobilizing the target molecules or biological entities in discrete regions of the substrate surface. The labeling of biological molecules or other biological entities with nonlinear-active labels allows a direct optical means of detecting interactions between the labeled biological molecule or entity and another molecule or entity (i.e. the test entity) in cases where the interaction results in a change in orientation or conformation of the biological molecule or entity using a surface-selective nonlinear optical technique.

In alternative aspects of the methods and systems described herein, at least two distinguishable nonlinear-active labels are used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the optical interface are used, with the resulting emanation of at least two nonlinear light beams.

Examples of nonlinear-active tags or labels include, but are not limited to, the compounds listed in Table 1, and their derivatives.

TABLE 1

| Examples of Nonlinear-Active Tags | | |
|---|---|---|
| 2-aryl-5-(4-pyridyl)oxazole | Hemicyanines | Polyimides |
| 2-(4-pyridyl)-cycloalkano[d]oxazoles | Indandione-1,3-pyidinium betaine | Polymethacrylates |
| 5-aryl-2-(4-pyridyl)oxazole | Indodicarbocyanines | PyMPO (pyridyloxazole) |
| 7-Hydroxycoumarin-3-carboxylic acid, succinimidyl ester | Melamines | PyMPO, succinimidyl ester (1-(3-(succinimidyloxy-carbonyl)benzyl)-4-(5-(4-PyMPO, maleimide |
| Azo dyes | Merocyanines | Stilbazims |
| Benzooxazoles | Methoxyphenyl)oxazol-2-yl)pyridinium bromide) | Stilbenes |
| Bithiophenes | Methylene blue | Stryryl-based dyes |
| Cyanines | Oxazole or oxadizole molecules | Sulphonyl-substituted azobenzenes |
| Dapoxyl carboxylic acid, succinimidyl ester | Oxonols | Thiophenes |
| Diaminobenzene compounds | Perylenes | Tricyanovinyl aniline |
| Diazostilbenes | Phenothiazine-stilbazole | Tricyanovinyl azo |
| Fluoresceins | Polyenes | |

In evaluating whether a species may be nonlinear-active, the following characteristics can indicate the potential for nonlinear activity: a large difference dipole moment (difference in dipole moment between the ground and excited states of the molecule), a large Stokes shift in fluorescence, or an aromatic or conjugated bonding character. In further evaluating such a species, an experimenter can use a simple technique known to those skilled in the art to confirm the nonlinear activity, for example, through detection of SHG from an air-water interface on which the nonlinear-active species has been distributed. Once a suitable nonlinear-active species has been selected for the experiment at hand, the species can be conjugated, if desired, to a biological molecule or entity for use in the surface-selective nonlinear optical methods and systems disclosed herein.

The following reference and references therein describe techniques available for creating a labeled biological entity from a synthetic dye and many other molecules: Greg T. Hermanson, Bioconjugate Techniques, Academic Press, New York, 1996.

In a specific aspect of the methods and systems disclosed, metal nanoparticles and assemblies thereof are modified to create biological nonlinear-active labels. The following references describe the modification of metal nanoparticles and assemblies: J. P. Novak and D. L. Feldheim, "Assembly of Phenylacetylene-Bridged Silver and Gold Nanoparticle Arrays", J. Am. Chem. Soc. 122:3979-3980 (2000); J. P. Novak, et al., "Nonlinear Optical Properties of Molecularly Bridged Gold Nanoparticle Arrays", J. Am. Chem. Soc. 122:12029-12030 (2000); Vance, F. W., Lemon, B. I., and Hupp, J. T., "Enormous Hyper-Rayleigh Scattering from Nanocrystalline Gold Particle Suspensions", J. Phys. Chem. B 102:10091-93 (1999).

In yet another aspect of the methods and systems disclosed herein, the nonlinear activity of the system can also be manipulated through the introduction of nonlinear analogues to molecular beacons, that is, molecular beacon probes that have been modified to incorporate a nonlinear-active label (or modulator thereof) instead of fluorophores and quenchers. These nonlinear optical analogues of molecular beacons are referred to herein as molecular beacon analogues (MB analogues or MBA). The MB analogues to be used in the described methods and systems can be synthesized according to procedures known to one of ordinary skill in the art.

Types of Biological Interactions Detected

The methods and systems disclosed herein provide for detection of a variety of interactions between biological entities, or between biological entities and test entities, depending on the choice of biological entities, test entities, and non-linear active labeling technique employed. In one aspect, the present disclosure provides for the qualitative detection of binding events, e.g. the binding of a ligand to a receptor, as indicated by the resulting conformational change induced in the receptor. In another aspect, the present disclosure provides for quantitative analysis of binding events, e.g. the binding of a ligand to a receptor, by performing replicate measurements using different concentrations of the ligand molecule and generating a dose-response curve using the percent change in maximal conformational change observed. Similarly, other aspects of the present disclosure may provide methods for qualitative or quantitative measurements of enzyme-inhibitor interactions, antibody-antigen interactions, the formation of complexes of biological macromolecules, or interactions of receptors with allosteric modulators.

In other specific embodiments, MB analogues can be used according to the methods disclosed herein as hybridization probes that can detect the presence of complementary nucleic acid target without having to separate probe-target hybrids from excess probes as in solution-phase hybridization assays, and without the need to label the targets oligonucleotides. MB analogue probes can also be used for the detection of RNAs within living cells, for monitoring the synthesis of specific nucleic acids in sample aliquots drawn from bioreactors, and for the construction of self-reporting oligonucleotide arrays. They can be used to perform homogeneous one-well assays for the identification of single-nucleotide variations in DNA and for the detection of pathogens or cells immobilized to surfaces for interfacial detection.

Interactions between biological entities or biological and test entities (e.g. binding reactions, conformational changes, etc.) can be correlated through the methods presently disclosed to the following measurable nonlinear signal parameters: (i) the intensity of the nonlinear light, (ii) the wavelength or spectrum of the nonlinear light, (iii) the polarization of the nonlinear light, (iv) the time-course of (i), (ii), or (iii), and/or vi) one or more combinations of (i), (ii), (iii), and (iv).

Laser Light Sources and Excitation Optical System

Figure 5:
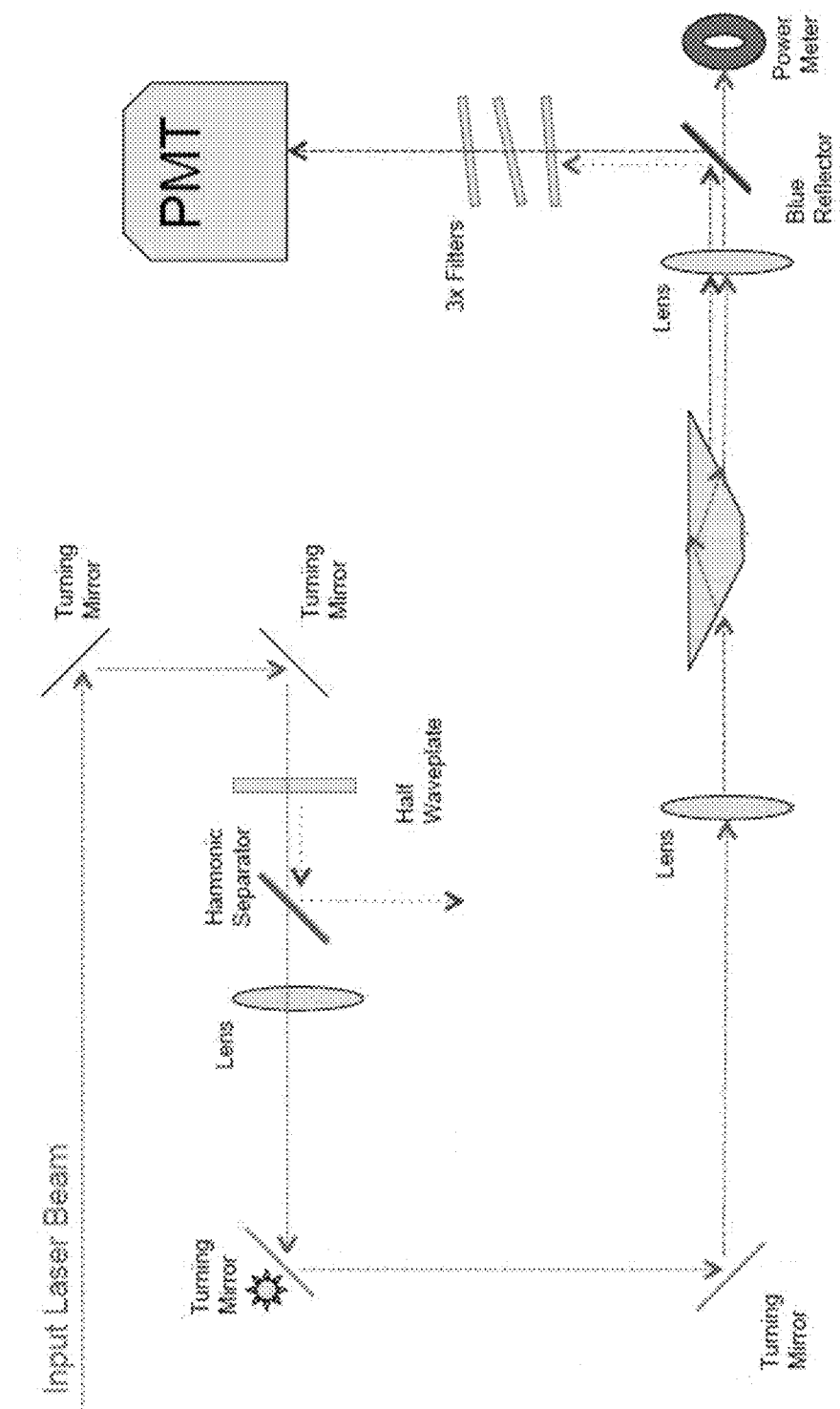
FIG. 5 shows a schematic for one example of an optical setup used for analysis of conformational change in biological molecules using nonlinear optical detection.
Figure 6:
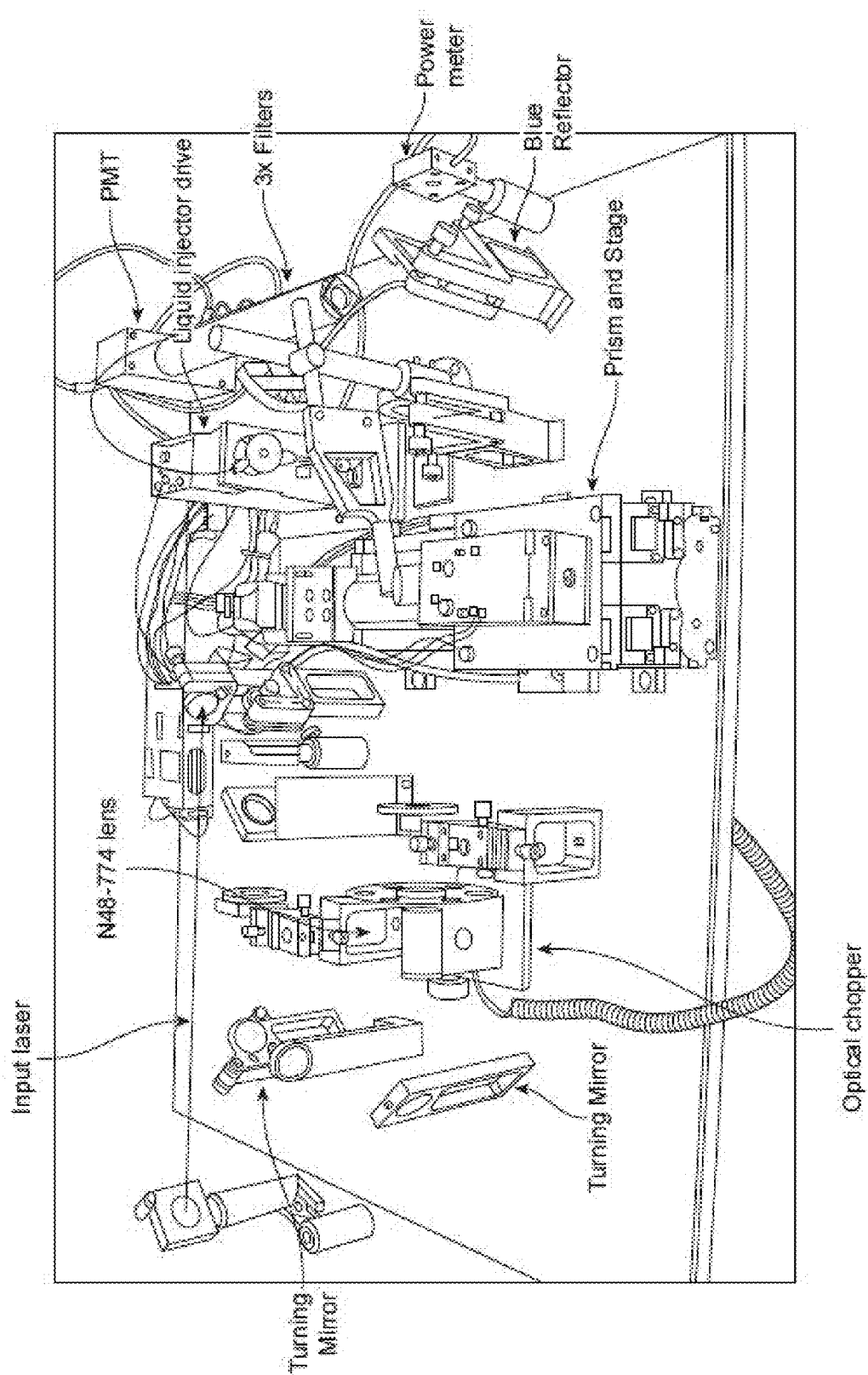
FIG. 6 shows a photograph of an optical setup used for analysis of conformational change in biological molecules using nonlinear optical detection.

FIG. 5 illustrates one aspect of the methods and systems disclosed herein wherein second harmonic light is generated by reflecting incident fundamental excitation light from the surface of a substrate comprising the sample interface (or optical interface). FIG. 6 shows a photograph of one example of a suitable optical setup. A laser provides the fundamental light necessary to generate second harmonic light at the sample interface. Typically this will be a picosecond or femtosecond laser, either wavelength tunable or not tunable, and commercially available (e.g. a Ti: Sapphire femtosecond laser or fiber laser system). Light at the fundamental frequency (w) exits the laser and its polarization is selected using, for example a half-wave plate appropriate to the frequency and intensity of the light (e.g., available from Melles Griot, Oriel, or Newport Corp.). The beam then passes through a harmonic separator designed to pass the fundamental light but block nonlinear light (e.g. second harmonic light). This filter is used to prevent back-reflection of the second harmonic beam into the laser cavity which can cause disturbances in the lasing properties. A combination of mirrors and lenses are then used to steer and shape the beam prior to reflection from a final mirror that directs the beam via a prism to impinge at a specific location and with a specific angle $\theta$ on the substrate surface such that it undergoes total internal reflection at the substrate surface. One of the mirrors in the optical path can be scanned if required using a galvanometer-controlled mirror scanner, a rotating polygonal mirror scanner, a Bragg diffractor, acousto-optic deflector, or other means known in the art to allow control of a mirror's position. The substrate comprising the optical interface and nonlinear-active sample surface can be mounted on an x-y translation stage (computer controlled) to select a specific location on the substrate surface for generation of the second harmonic beam. In some aspects of the methods and systems presently described, it is desirable to scan or rotate one mirror in order to slightly vary the angle of incidence for total internal reflection, and thereby maximize the nonlinear optical signal emitted from the discrete regions of the substrate surface without substantially changing the position of the illuminating excitation light spot. In some aspects, two (or more) lasers having different fundamental frequencies may be used to generate sum frequency or difference frequency light at the optical interface on which the non-linear active sample is immobilized.

Substrate Formats, Optical Interface, and Total Internal Reflection

As described above, the systems and methods of the present disclosure utilize a planar substrate for immobilization of one or more biological entities on a top surface of the substrate, wherein the top substrate surface further comprises the optical interface (or sample interface) used for exciting nonlinear optical signals. The substrate can be glass, silica, fused-silica, plastic, or any other solid material that is transparent to the fundamental and second harmonic light beams, and that supports total internal reflection at the substrate/sample interface when the excitation light is incident at an appropriate angle. In some aspects of the invention, the discrete regions within which biological entities are contained are configured as one-dimensional or two-dimensional arrays, and are separated from one another by means of a hydrophobic coating or thin metal layer. In other aspects, the discrete regions may comprise indents in the substrate surface. In still other aspects, the discrete regions may be separated from each other by means of a well-forming component such that the substrate forms the bottom of a microwell plate (or microplate), and each individual discrete region forms the bottom of one well in the microwell plate. In one aspect of the present disclosure, the well-forming component separates the top surface of the substrate into 96 separate wells. In another aspect, the well-forming component separates the top surface of the substrate into 384 wells. In yet another aspect, the well-forming component separates the top surface of the substrate into 1,536 wells. In all of these aspects, the substrate, whether configured in a planar array, indented array, or microwell plate format, may comprise a disposable or consumable device or cartridge that interfaces with other optical and mechanical components of the high throughput system.

The methods and systems disclosed herein further comprise specifying the number of discrete regions or wells into which the substrate surface is divided, irrespective of how separation is maintained between discrete regions or wells. Having larger numbers of discrete regions or wells on a substrate may be advantageous in terms of increasing the sample analysis throughput of the method or system. In one aspect of the present disclosure, the number of discrete regions or wells per substrate is between 10 and 1,600. In other aspects, the number of discrete regions or wells is at least 10, at least 20, at least 50, at least 100, at least 200, at least 300, at least 400, at least 500, at least 750, at least 1,000, at least 1,250, at least 1,500, or at least 1,600. In yet other aspects of the disclosed methods and systems, the number of discrete regions or wells is at most 1,600, at most 1,500, at most 1,000, at most 750, at most 500, at most 400, at most 300, at most 200, at most 100, at most 50, at most 20, or at most 10. In a preferred aspect, the number of discrete regions or wells is 96. In another preferred aspect, the number of discrete regions or wells is 384. In yet another preferred aspect, the number of discrete regions or wells is 1,536. Those of skill in the art will appreciate that the number of discrete regions or wells may fall within any range bounded by any of these values (e.g. from about 12 to about 1,400).

The methods and systems disclosed herein also comprise specifying the surface area of the discrete regions or wells into which the substrate surface is divided, irrespective of how separation is maintained between discrete regions or wells. Having discrete regions or wells of larger area may facilitate ease-of-access and manipulation of the associated biological entities in some cases, whereas having discrete regions or wells of smaller area may be advantageous in terms of reducing assay reagent volume requirements and increasing the sample analysis throughput of the method or system. In one aspect of the present disclosure, the surface area of the discrete regions or wells is between 1 mm$^2$ and 100 mm$^2$. In other aspects, the area of the discrete regions or wells is at least 1 mm$^2$, at least 2.5 mm$^2$, at least 5 mm$^2$, at least 10 mm$^2$, at least 20 mm$^2$, at least 30 mm$^2$, at least 40 mm$^2$, at least 50 mm$^2$, at least 75 mm$^2$, or at least 100 mm$^2$. In yet other aspects of the disclosed methods and systems, the area of the discrete regions or wells is at most 100 mm$^2$, at most 75 mm$^2$, at most 50 mm$^2$, at most 40 mm$^2$, at most 30 mm$^2$, at most 20 mm$^2$, at most 10 mm$^2$, at most 5 mm$^2$, at most 2.5 mm$^2$, or at most 1 mm$^2$. In a preferred aspect, the area of discrete regions or wells is about 35 mm$^2$. In another preferred aspect, the area of the discrete regions or wells is about 8.6 mm$^2$. Those of skill in the art will appreciate that the area of the discrete regions or wells may fall within any range bounded by any of these values (e.g. from about 2 mm$^2$ to about 95 mm$^2$).

Discrete regions of the substrate surface are sequentially exposed to (illuminated with) excitation light by re-positioning the substrate relative to the excitation light source. Total internal reflection of the incident excitation light creates an "evanescent wave" at the sample interface, which excites the nonlinear-active label and results in generation of second harmonic light (or in some aspects, sum frequency or difference frequency light). Because the intensity of the evanescent wave, and hence the intensity of the nonlinear optical signals generated, is dependent on the incident angle of the excitation light beam, precise orientation of the substrate plane with respect to the optical axis of the excitation beam and efficient optical coupling of the beam to the substrate is critical for achieving optimal SHG signal across the array of discrete regions. In some aspects of the present disclosure, total internal reflection is achieved by means of a single reflection of the excitation light from the substrate surface. In other aspects, the substrate may be configured as a waveguide such that the excitation light undergoes multiple total internal reflections as it propagates along the waveguide. In yet other aspects, the substrate may be configured as a zero-mode waveguide, wherein an evanescent field is created by means of nanofabricated structures.

Figure 7:
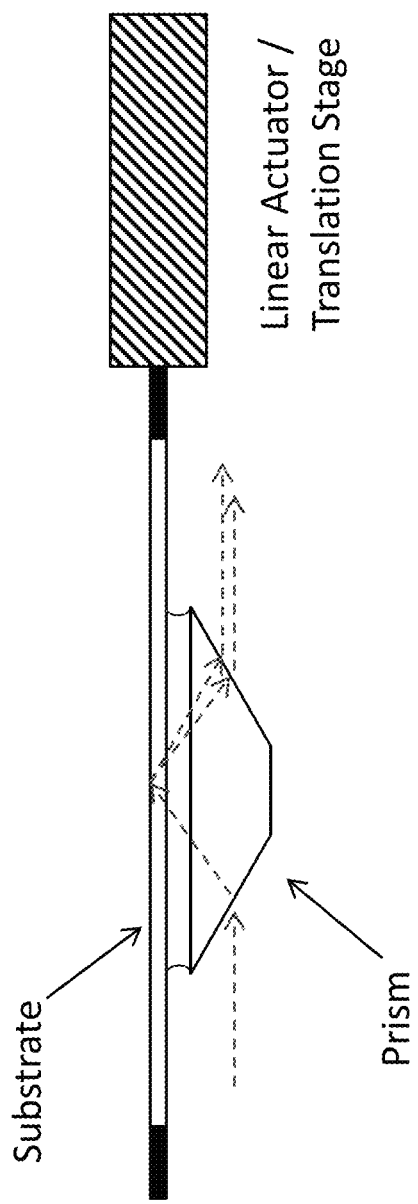
FIG. 7 shows a schematic illustration depicting the use of a prism to direct excitation light at an appropriate incident angle such that the excitation light undergoes total internal reflection at the top surface of a substrate. The two dashed lines to the right of the prism indicate the optical path of the reflected excitation light and the nonlinear optical signal generated at the substrate surface when nonlinear-active species are tethered to the surface. The substrate is optionally connected to the actuator of an X-Y translation stage for re-positioning between measurements. The curved lines between the top surface of the prism and the lower surface of the substrate indicate the presence a thin layer (not to scale) of index-matching fluid used to ensure high optical coupling efficiency between the prism and substrate.

Efficient optical coupling between the excitation light beam and the substrate in an optical setup such as the one illustrated in FIGS. 5 and 7 would typically be achieved by use of an index-matching fluid such as mineral oil, mixtures of mineral oil and hydrogenated terphenyls, perfluorocarbon fluids, glycerin, glycerol, or similar fluids having a refractive index near 1.5, wherein the index-matching fluid is wicked between the prism and the lower surface of the substrate. Since a static, bubble-free film of index-matching fluid is likely to be disrupted during fast re-positioning of the substrate, the systems and methods disclosed herein include alternative approaches for creating efficient optical coupling of the excitation beam to the substrate in high throughput systems.

Figure 8:
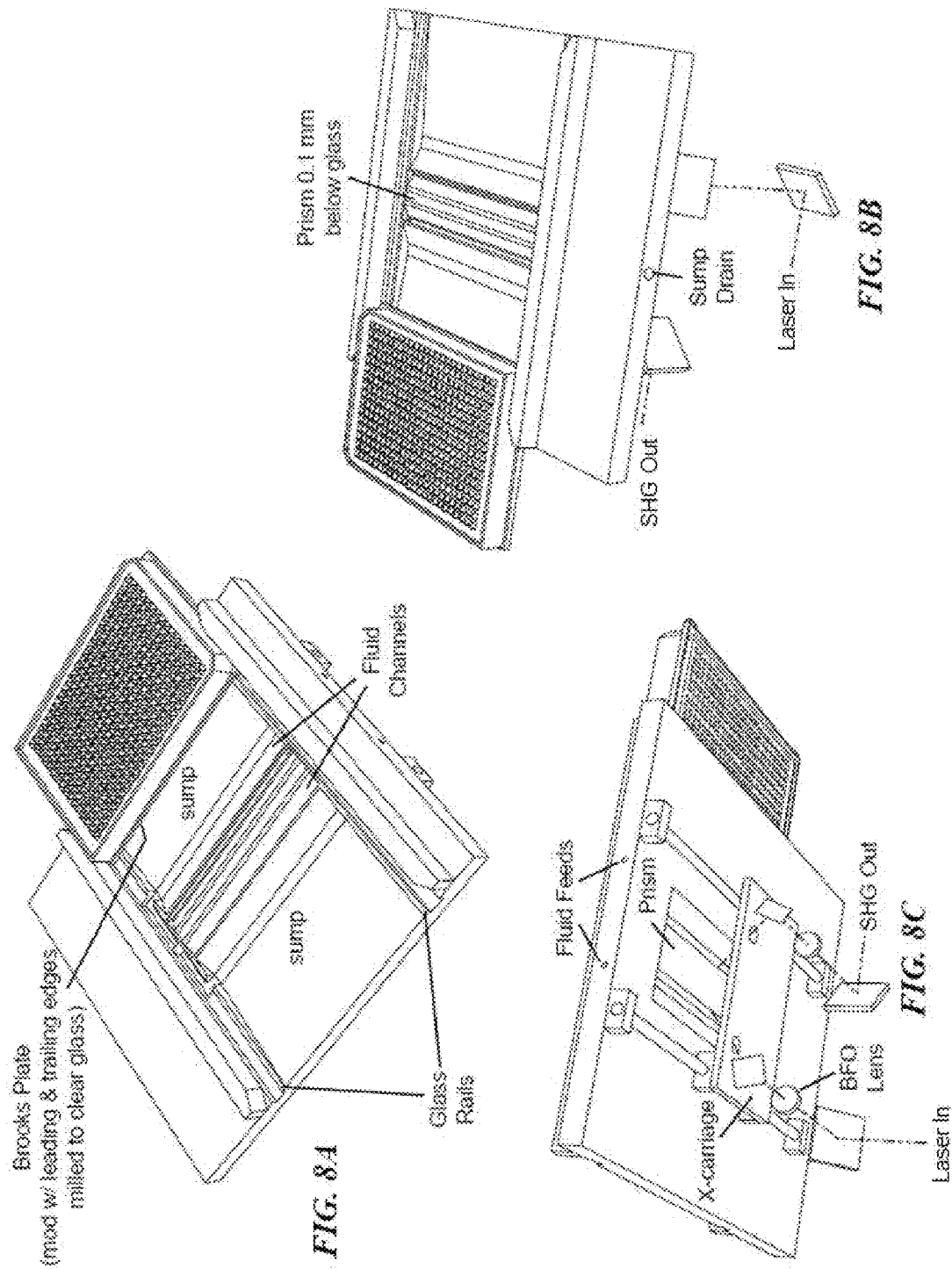
FIGS. 8A-C show different views of one exemplary design concept for a system that uses a continuously recirculating flow of index-matching fluid to provide high optical coupling efficiency between the prism (attached to the optical instrument in this example) and the substrate (configured as the transparent bottom of a microwell plate in this example). The substrate (microwell plate) is free to translate relative to the prism while a continuous flow of index-matching fluid provided by the indicated fluid channels ensures good optical coupling of excitation light with the substrate.

FIG. 8 illustrates one aspect of a high throughput system of the present disclosure in which a continuously recirculating stream of index-matching fluid is used to maintain efficient optical coupling between the prism, which is mounted as part of the optical system, and the substrate, which is configured in a microwell plate format (e.g. a glass bottom microplate format) and is free to translate relative to the prism. The continuous flow of index-matching fluid in this case ensures that the thin film of fluid between the prism and substrate is never disrupted as the two components move relative to each other, i.e. any small bubbles or discontinuities in the thin layer of fluid will be eliminated or pushed out from the gap between the prism and substrate by means of the fluid flow. Index-matching fluid is introduced into the gap via the two fluid channels indicated in the drawing, and may be collected in a suitable reservoir or sump, from which it may be recirculated using a small pump. In an alternative implementation of the same concept, instead of the line-contact between substrate and prism indicated in FIG. 8, point contact between a single discrete region and a cylindrical total internal reflection (TIR) probe would be utilized, where the index-matching fluid would flow up through a center fluid channel, and then down over the sides of the cylindrical TIR probe to be collected in a suitable reservoir or sump.

Figure 9:
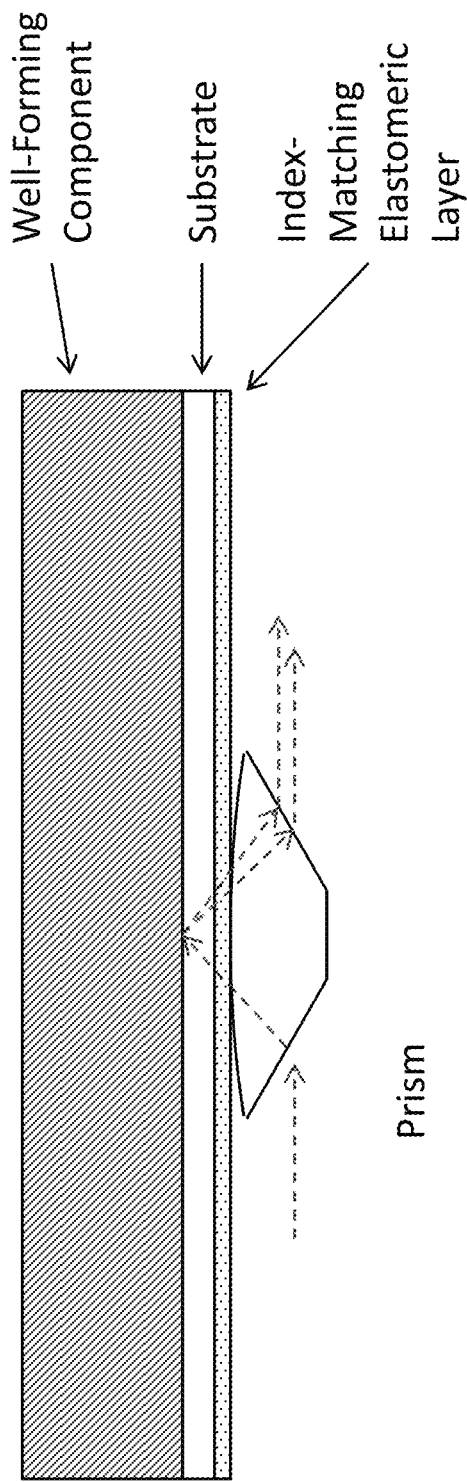
FIG. 9 shows a schematic illustration depicting the use of a layer of index-matching elastomeric material attached or adjacent to the lower surface of a transparent substrate (configured in a microwell plate format in this example) to ensure high optical coupling efficiency between a prism and the upper surface of the substrate. In some embodiments of this approach, the upper surface of the prism is slightly domed to focus the compression force when bringing the microwell plate and prism into contact, thereby reducing or eliminating the formation of air gaps between the prism and elastomeric material.
Figure 10A:
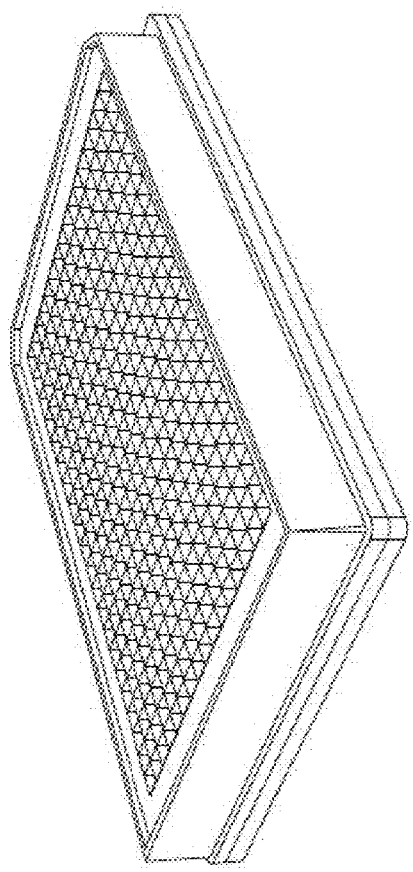
FIGS. 10A-B illustrate a microwell plate with integrated prism array for providing good optical coupling of the excitation light to the top surface of the substrate. In this approach, the prism indicated in the schematic illustrations of FIGS. 4, 5, 7, and 9 are replaced by the prism array attached to the underside of the substrate.
Figure 10B:
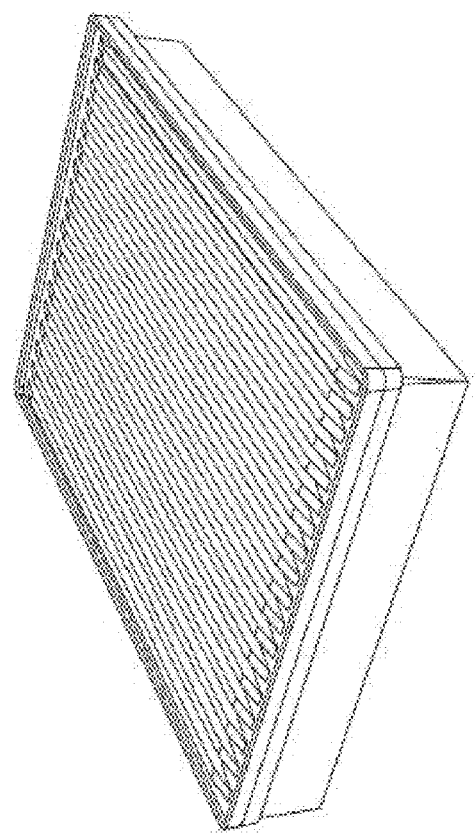
Figure 10C:
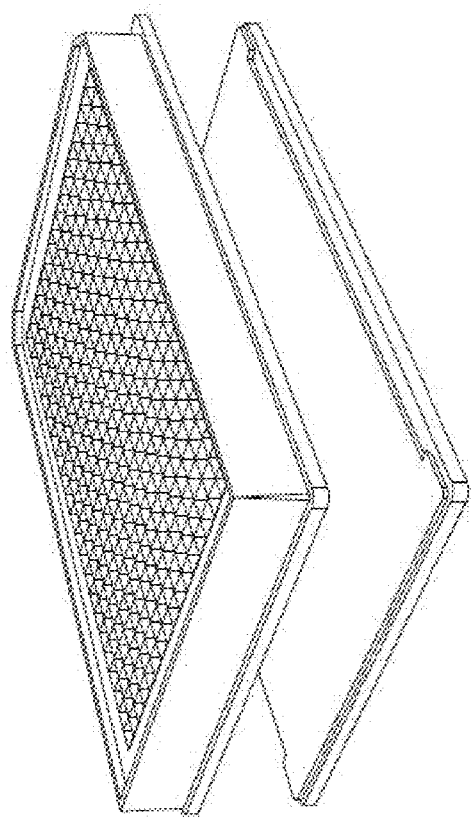
FIGS. 10C-D show exploded views of the microwell plate device shown in FIGS. 10A-B.
Figure 10D:
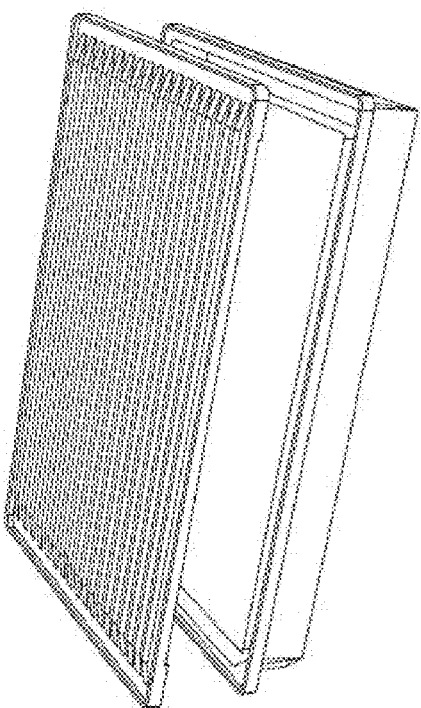

FIG. 9 illustrates another aspect of a high throughput system of the present disclosure, in which a thin layer of index-matching elastomeric material is used in place of index-matching fluid to maintain efficient optical coupling between the prism and substrate. In this case, the substrate is again packaged in a microwell plate format (e.g. a glass bottom microplate format), but with a thin layer of an index-matching elastomeric material attached to or adjacent to the lower surface of the substrate, such that when placed in contact with the upper surface of the prism, the elastomer fills the gap between prism and substrate and provides for efficient optical coupling. Examples of elastomeric materials that may be used include, but are not limited to silicones having a refractive index of about 1.4. In one aspect of the present disclosure, the refractive index of the elastomeric material is between about 1.35 and about 1.6. In other aspects, the index of refraction is about 1.6 or less, about 1.55 or less, about 1.5 or less, about 1.45 or less, about 1.4 or less, or about 1.35 or less. In yet other aspects, the index of refraction is at least about 1.35, at least about 1.4, at least about 1.45, at least about 1.5, at least about 1.55, or at least about 1.6. Those of skill in the art will appreciate that the index of refraction of the elastomeric layer may fall within any range bounded by any of these values (e.g. from about 1.4 to about 1.6). In one aspect of this approach, the thickness of the layer of elastomeric material is between about 0.1 mm and 2 mm. In other aspects, the thickness of the elastomeric layer is at least 0.1 mm, at least 0.2 mm, at least 0.4 mm, at least 0.6 mm, at least 0.8 mm, at least 1.0 mm, at least 1.2 mm, at least 1.4 mm, at least 1.6 mm, at least 1.8 mm, or at least 2.0 mm. In another aspect of this approach, the thickness of the elastomeric layer is at most 2.0 mm, at most 1.8 mm, at most 1.6 mm, at most 1.4 mm, at most 1.2 mm, at most 1.0 mm, at most 0.8 mm, at most 0.6 mm, at most 0.4 mm, at most 0.2 mm, or at most 0.1 mm. Those of skill in the art will appreciate that the thickness of the elastomeric layer my fall within any range bounded by any of these values (e.g. from about 0.1 mm to about 1.5 mm). In another aspect of this approach, the upper surface of the prism has a partially-cylindrical ridge or is domed (FIG. 9) to focus the compression force and provide better contact between substrate, elastomeric layer, and prism surface. This approach may also require the use of a third axis of translation for positioning of the substrate, i.e. between excitation and detection steps, the substrate (microwell plate) would be raised slightly to eliminate contact between the elastomeric layer and the prism prior to re-positioning the substrate to the location of the next discrete region to be analyzed.

Figure 11:
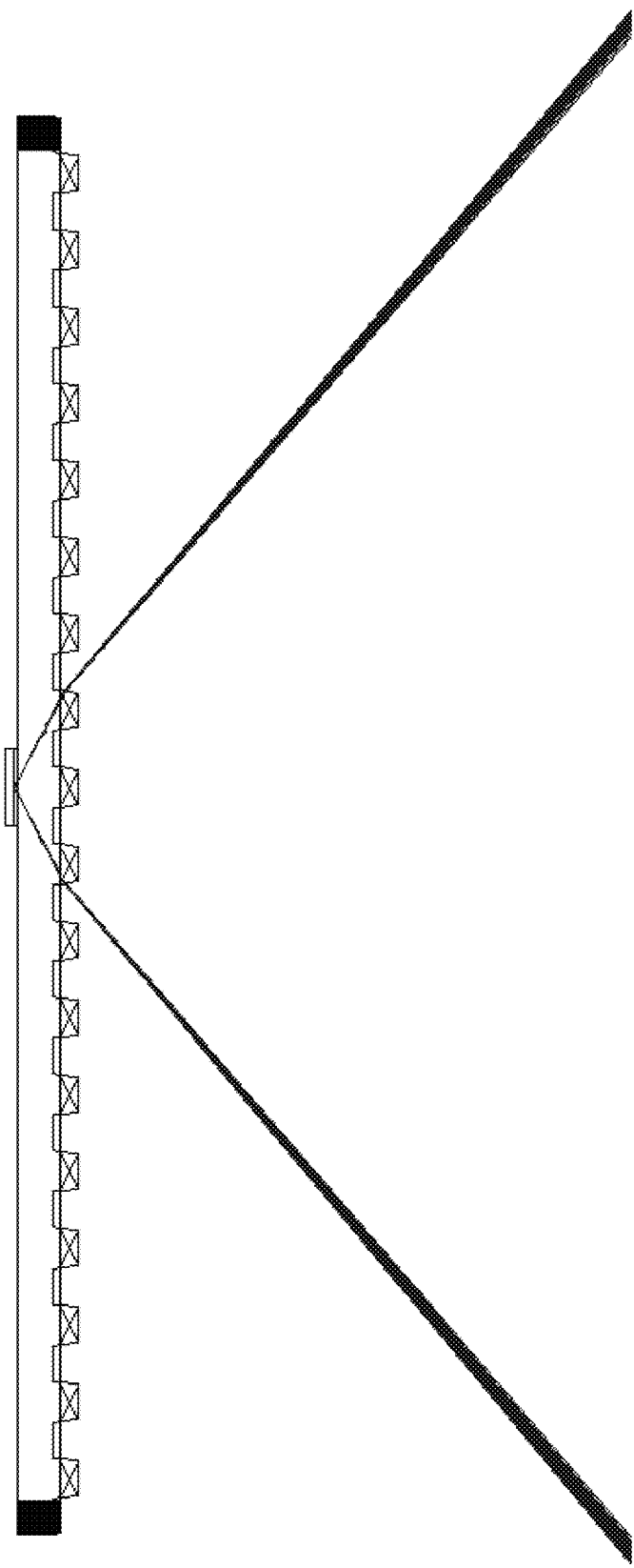
FIG. 11 illustrates the incident and exit light paths for coupling the excitation light to the substrate surface via total internal reflection using the design concept illustrated in FIGS. 10A-B.

FIGS. 10A-D illustrate a preferred aspect of a high throughput system of the present disclosure, in which an array of prisms or gratings is integrated with the lower surface of the substrate (packaged in a microwell plate format) and used to replace the fixed prism, thereby eliminating the need for index-matching fluids or elastomeric layers entirely. The array of prisms (or gratings) is aligned with the array of discrete regions or wells on the upper surface of the substrate in such a way that incident excitation light is directed by an "entrance prism" ("entrance grating") to a discrete region or well that is adjacent to but not directly above the entrance prism (entrance grating), at an angle of incidence that enables total internal reflection of the excitation light beam from the sample interface (see FIG. 11), and such that the reflected excitation beam, and nonlinear-optical signals generated at the illuminated discrete region, are collected by an "exit prism" ("exit grating") that is again offset from (adjacent to but not directly underneath) the discrete region under interrogation, and wherein the entrance prism and exit prism (entrance grating and exit grating) for each discrete region are different, non-unique elements of the array.

In general, for an array of discrete regions comprising M rows×N columns of individual features, the corresponding prism or grating array will have M+2 rows×N columns or N+2 columns×M rows of individual prisms or gratings. In some embodiments, M may have a value of at least 2, at least 4, at least 6, at least 8, at least 12, at least 14, at least 16, at least 18, at least 20, at least 25, at least 30, at least 35, at least 40, at least 45, or at least 50 rows. In some embodiments, M may have a value of at most 50, at most 45, at most 40, at most 35, at most 30, at most 25, at most 20, at most 18, at most 16, at most 14, at most 12, at most 10, at most 8, at most 6, at most 4, or at most 2 rows. Similarly, in some embodiments, N may have a value of at least 2, at least 4, at least 6, at least 8, at least 12, at least 14, at least 16, at least 18, at least 20, at least 25, at least 30, at least 35, at least 40, at least 45, or at least 50 columns. In some embodiments, N may have a value of at most 50, at most 45, at most 40, at most 35, at most 30, at most 25, at most 20, at most 18, at most 16, at most 14, at most 12, at most 10, at most 8, at most 6, at most 4, or at most 2 columns. As will be apparent to those of skill in the art, M and N may have the same value or different values, and may have any value within the range specified above, for example, M=15 and N=45.

Figure 12:
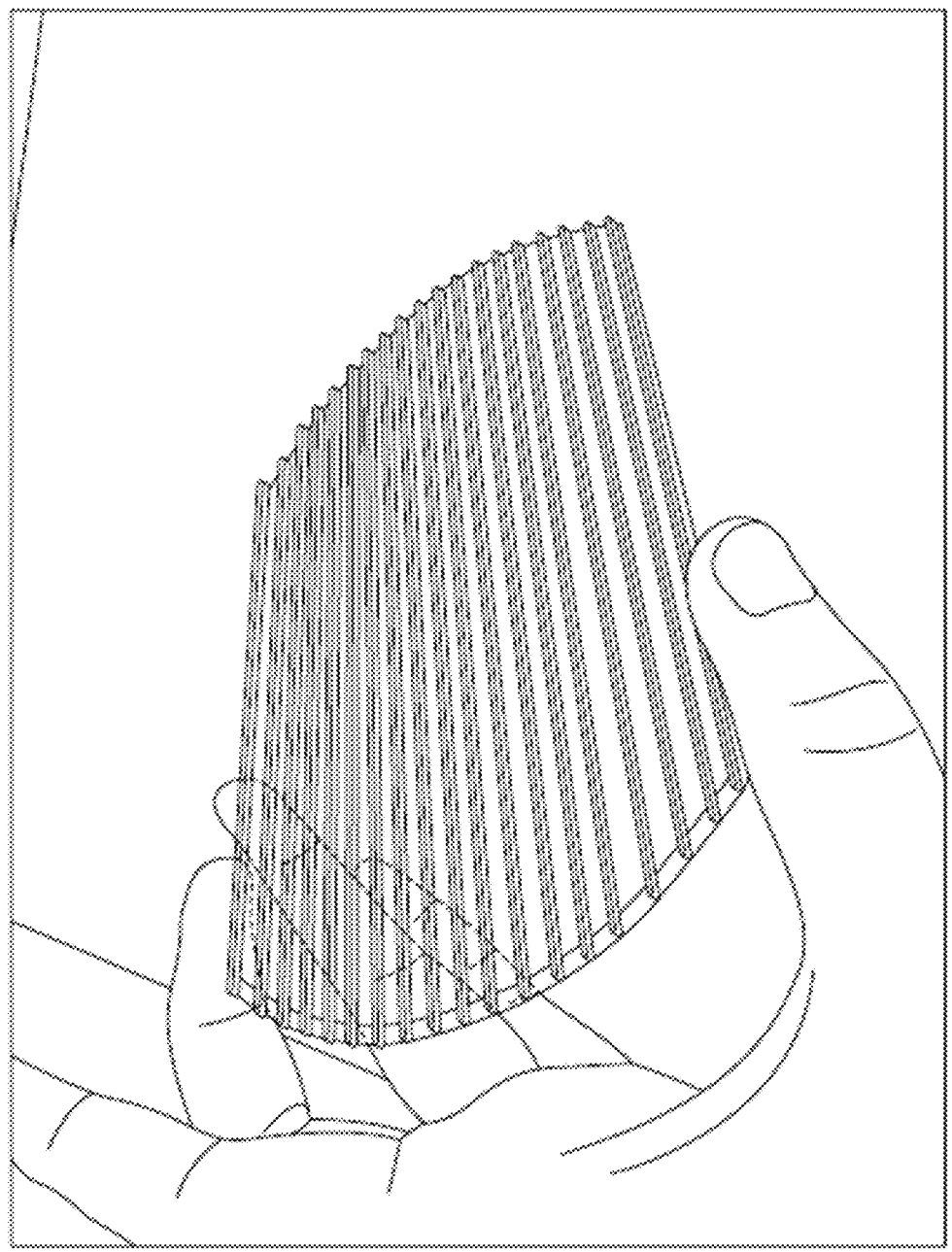
FIG. 12 shows a photograph of a prototype for the prism array design concept illustrated in FIGS. 10A-B.

The geometry and dimensions of the individual prisms or gratings, including the thickness of the prism or grating array layer, are optimized to ensure that incident light undergoes total internal reflection at the selected discrete region of the substrate, and nonlinear optical signals generated at the selected discrete region are collected, with high optical coupling efficiency, independently of the position of substrate (microwell plate) relative to the excitation light beam. FIG. 12 shows a photograph of a prism array prototype. The prism or grating arrays may be fabricated by a variety of techniques known to those of skill in the art, for example, in a preferred aspect, they may be injection molded from smooth flowing, low birefringence materials such as cyclic olefin copolymer (COC) or cyclic olefin polymer (COP), acrylic, polyester, or similar polymers. In some aspects, the prism or grating array may be fabricated as a separate component, and subsequently integrated with the lower surface of the substrate. In other aspects, the prism or grating array may be fabricated as an integral feature of substrate itself.

Immobilization Chemistries

As disclosed herein, substrates in any of the formats described above are further configured for immobilization of biological entities within the specified discrete regions. Immobilization of biological molecules or cells may be accomplished by a variety of techniques known to those of skill in the art, for example, through the use of aminopropyl silane chemistries to functionalize glass or fused-silica surfaces with amine functional groups, followed by covalent coupling using amine-reactive conjugation chemistries, either directly with the biological molecule of interest, or via an intermediate spacer or linker molecule. Non-specific adsorption may also be used directly or indirectly, e.g. through the use of BSA-NHS (BSA-N-hydroxysuccinimide) by first attaching a molecular layer of BSA to the surface and then activating it with N,N'-disuccinimidyl carbonate. The activated lysine, aspartate or glutamate residues on the BSA react with surface amines on proteins.

In a preferred aspect of the present disclosure, biological molecules may be immobilized on the surface by means of tethering to or embedding in "supported lipid bilayers", the latter comprising small patches of lipid bilayer confined to a silicon or glass surface by means of hydrophobic and electrostatic interactions, where the bilayer is "floating" above the substrate surface on a thin layer of aqueous buffer. Supported phospholipid bilayers can also be prepared with or without membrane proteins or other membrane-associated components as described, for example, in Salafsky et al., "Architecture and Function of Membrane Proteins in Planar Supported Bilayers: A Study with Photosynthetic Reaction Centers", Biochemistry 35 (47): 14773-14781 (1996); Gennis, R., *Biomembranes*, Springer-Verlag, 1989; Kalb et al., "Formation of Supported Planar Bilayers by Fusion of Vesicles to Supported Phospholipid Monolayers", Biochimica Biophysica Acta. 1103:307-316 (1992); and Brian et al. "Allogeneic Stimulation of Cytotoxic T-cells by Supported Planar Membranes", PNAS-Biological Sciences 81(19): 6159-6163 (1984), relevant portions of which are incorporated herein by reference. Supported phospholipid bilayers are well known in the art and there are numerous techniques available for their fabrication. Supported bilayers should typically be submerged in aqueous solution to prevent their destruction when exposed to air.

Collection Optics and Detector

FIG. 5 further illustrates the collection optics and detector used to detect nonlinear optical signals generated upon sequential illumination of the discrete regions of the substrate. Because surface-selective nonlinear optical techniques are coherent techniques, meaning that the fundamental and nonlinear optical light beams have wave fronts that propagate through space with well-defined spatial and phase relationships, minimal collection optics are required. Emitted nonlinear optical signals are collected by means of a prism (or the integrated prism or grating array of the microplate device described above) and directed via a dichroic reflector and mirror to the detector. Additional optical components, e.g. lenses, optical bandpass filters, mirrors, etc. are optionally used to further shape, steer, and/or filter the beam prior to reaching the detector. A variety of different photodetectors may be used, including but not limited to, photodiodes, avalanche photodiodes, photomultipliers, CMOS sensors, or CCD devices.

X-Y Translation Stage

Figure 4:
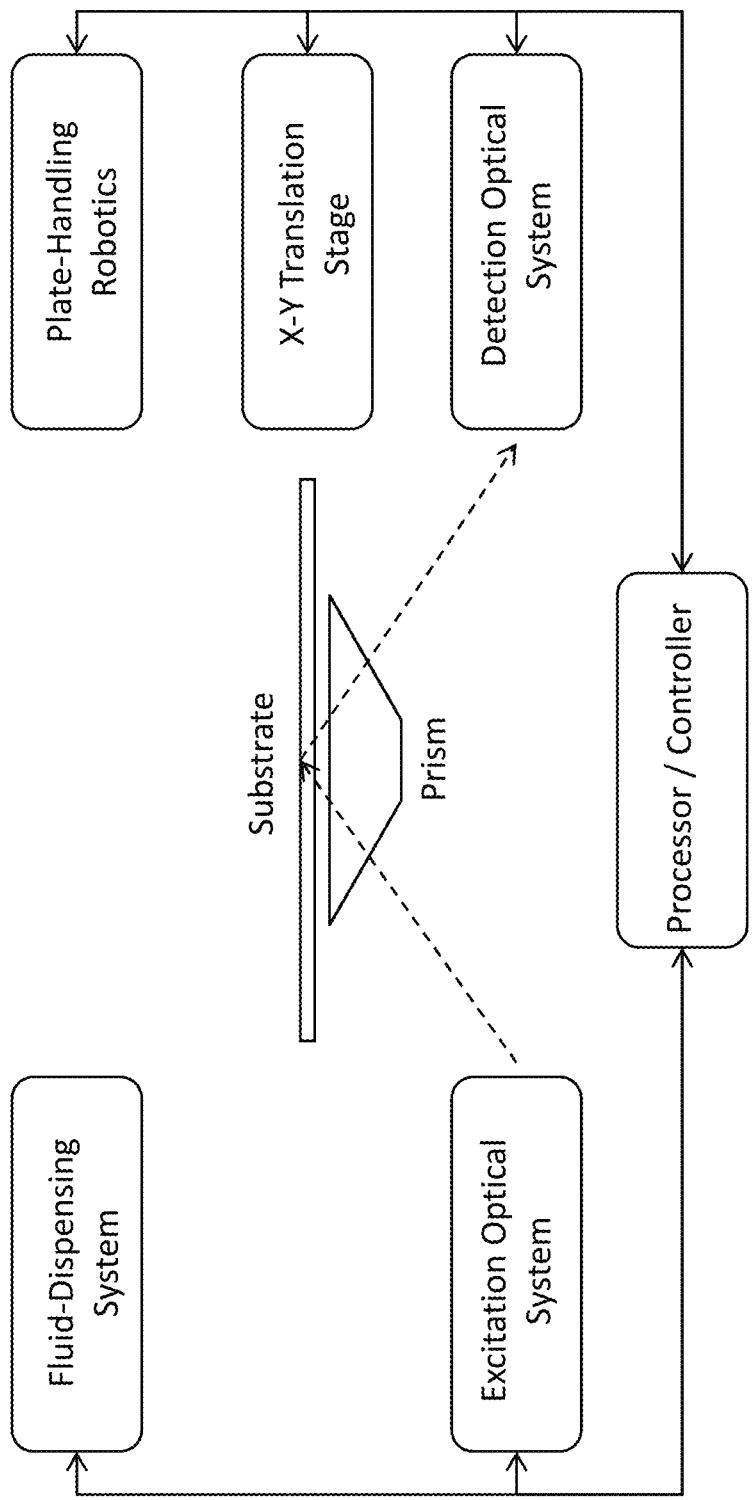
FIG. 4 illustrates one example of the system architecture for a high throughput analysis system for determining conformational change in biological molecules or other biological entities based on nonlinear optical detection.

As illustrated in FIG. 4, implementation of the high throughput systems disclosed herein ideally utilizes a high precision X-Y (or in some cases, an X—Y-Z) translation stage for re-positioning the substrate (in any of the formats described above) in relation to the excitation light beam. Suitable translation stages are commercially available from a number of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate measurements of nonlinear optical signals when interspersing repeated steps of optical detection and/or liquid-dispensing. Also, as the size of the focal spot for the excitation light [20-200 microns in diameter or on a side is substantially smaller than the size of the discrete regions on the substrate, in some aspects of the present disclosure, it may also be desirable to return to a slightly different position within a given discrete region when making replicate measurements, or to slowly scan the excitation beam across a portion of the discrete region over the course of a single measurement, thereby eliminating potential concerns regarding the photo-bleaching effects of long exposures or prior exposures.

Consequently, the methods and systems disclosed herein further comprise specifying the precision with which the translation stage is capable of positioning a substrate in relation to the excitation light beam. In one aspect of the present disclosure, the precision of the translation stage is between about 1 um and about 10 um. In other aspects, the precision of the translation stage is about 10 um or less, about 9 um or less, about 8 um or less, about 7 um or less, about 6 um or less, about 5 um or less, about 4 um or less, about 3 um or less, about 2 um or less, or about 1 um or less. Those of skill in the art will appreciate that the precision of the translation stage may fall within any range bounded by any of these values (e.g. from about 1.5 um to about 7.5 um).

Fluid Dispensing System

As illustrated in FIG. 4, some embodiments of the high throughput systems disclosed herein further comprise an automated, programmable fluid-dispensing (or liquid-dispensing) system for use in contacting the biological or target entities immobilized on the substrate surface with test entities (or test compounds), the latter typically being dispensed in solutions comprising aqueous buffers with or without the addition of a small organic solvent component, e.g. dimethylsulfoxide (DMSO). Suitable automated, programmable fluid-dispensing systems are commercially available from a number of vendors, e.g. Beckman Coulter, Perkin Elmer, Tecan, Velocity 11, and many others. In a preferred aspect of the systems and methods disclosed herein, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on the substrate.

Plate-Handling Robotics

In other aspects of the high throughput systems disclosed herein, the system further comprises a microplate-handling (or plate-handling) robotic system (FIG. 4) for automated replacement and positioning of substrates (in any of the formats described above) in relation to the optical excitation and detection optics, or for optionally moving substrates between the optical instrument and the fluid-dispensing system. Suitable automated, programmable microplate-handling robotic systems are commercially available from a number of vendors, including Beckman Coulter, Perkin Elemer, Tecan, Velocity 11, and many others. In a preferred aspect of the systems and methods disclosed herein, the automated microplate-handling robotic system is configured to move collections of microwell plates comprising immobilized biological entities and/or aliquots of test compounds to and from refrigerated storage units.

Processor/Controller and Constraint-Based Scheduling Algorithm

In another aspect of the present disclosure, the high throughput systems disclosed further comprise a processor (or controller, or computer system) (FIG. 4) configured to run system software which controls the various subsystems described (excitation and detection optical systems, X-Y (or X-Y-Z) translation stage, fluid-dispensing system, and plate-handling robotics) and synchronizes the different operational steps involved in performing high throughput conformational analysis. In addition to handling the data acquisition process, i.e. collection of output electronic signals from the detector that correspond to the nonlinear optical signals associated with conformational change, the processor or controller is also typically configured to store the data, perform data processing and display functions (including determination of whether or not changes in orientation or conformation have occurred for the biological entities, or combinations of biological and test entities, that have been tested), and operate a graphical user interface for interactive control by an operator. The processor or controller may also be networked with other processors, or connected to the internet for communication with other instruments and computers at remote locations.

Typical input parameters for the processor/controller may include set-up parameters such as the total number of microwell plates to be analyzed; the number of wells per plate; the number of times excitation and detection steps are to be performed for each discrete region of the substrate or well of the microplate (e.g. to specify endpoint assay or kinetic assay modes); the total timecourse over which kinetic data should be collected for each discrete region or well; the order, timing, and volume of test compound solutions to be delivered to each discrete region or well; the dwell time for collection and integration of nonlinear optical signals; the name(s) of output data files; and any of a number of system set-up and control parameters known to those skilled in the art.

In a preferred aspect of the present disclosure, the processor or controller is further configured to perform system throughput optimization by means of executing a constraint-based scheduling algorithm. This algorithm utilizes system set-up parameters as described above to determine an optimal sequence of interspersed excitation/detection and liquid-dispensing steps for discrete regions or wells that may or may not be adjacent to each other, such that the overall throughput of the system, in terms of number of biological entities and/or test entities analyzed per hour, is maximized. Optimization of system operational steps is an important aspect of achieving high throughput analysis. In some aspects of the disclosed methods and systems, the average throughput of the analysis system may range from about 10 test entities tested per hour to about 1,000 test entities tested per hour. In some aspects, the average throughput of the analysis system may be at least 10 test entities tested per hour, at least 25 test entities tested per hour, at least 50 test entities tested per hour, at least 75 test entities tested per hour, at least 100 test entities tested per hour, at least 200 test entities tested per hour, at least 400 test entities tested per hour, at least 600 test entities tested per hour, at least 800 test entities tested per hour, or at least 1,000 test entities tested per hour. In other aspects, the average throughput of the analysis system may be at most 1,000 test entities tested per hour, at most 800 test entities tested per hour, at most 600 test entities tested per hour, at most 400 test entities tested per hour, at most 200 test entities tested per hour, at most 100 test entities tested per hour, at most 75 test entities tested per hour, at most 50 test entities tested per hour, at most 25 test entities tested per hour, or at most 10 test entities tested per hour.

Computer Systems and Networks

In various embodiments, the methods and systems of the invention may further comprise software programs installed on computer systems and use thereof. Accordingly, as noted above, computerized control of the various subsystems and synchronization of the different operational steps involved in performing high throughput conformational analysis, including data analysis and display, are within the bounds of the invention.

Figure 21:
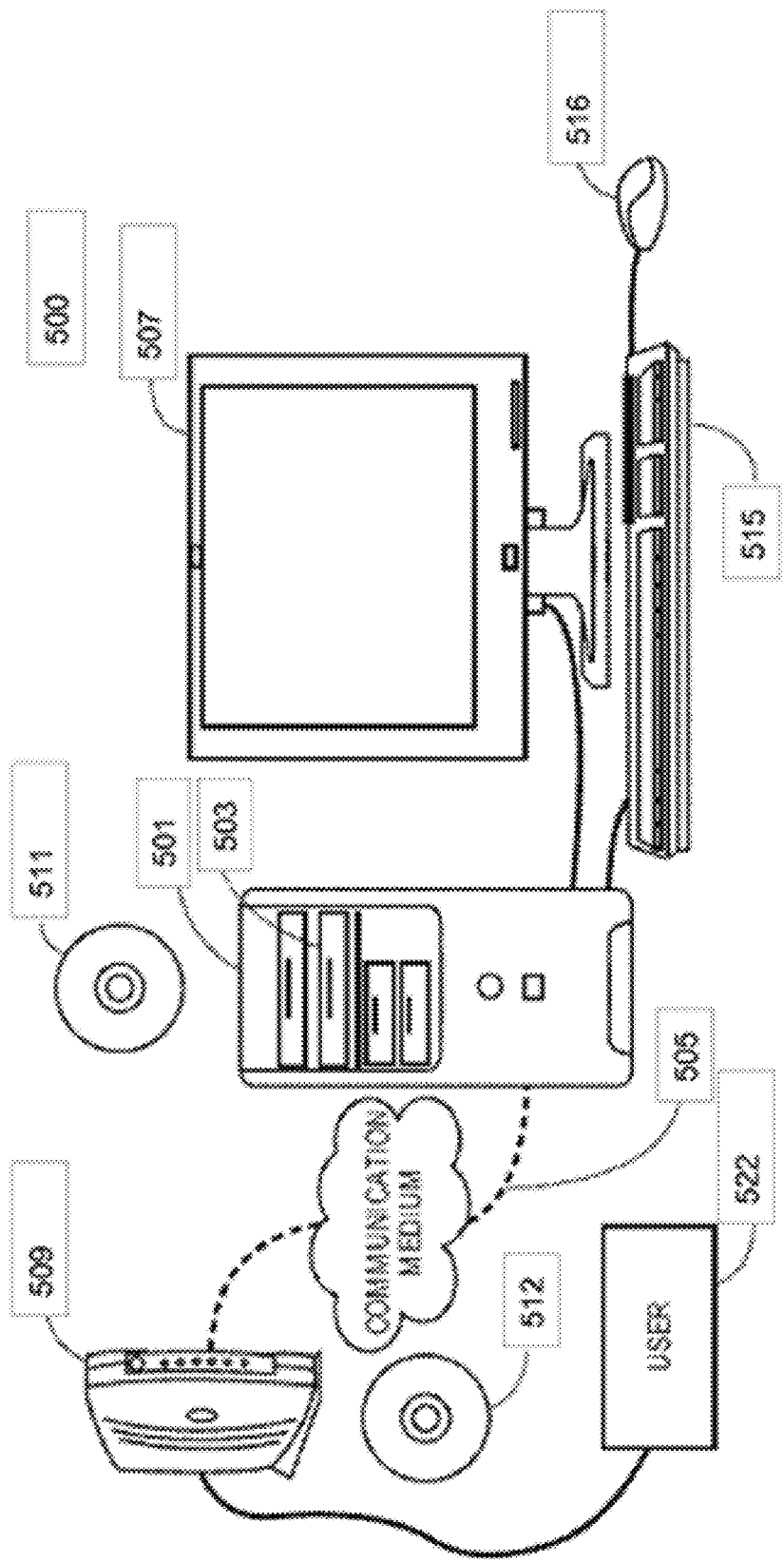
FIG. 21 illustrates a computer system that may be configured to control the operation of the systems disclosed herein.

The computer system 500 illustrated in FIG. 21 may be understood as a logical apparatus that can read instructions from media 511 and/or a network port 505, which can optionally be connected to server 509 having fixed media 512. The system, such as shown in FIG. 21 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 21.

Figure 22:
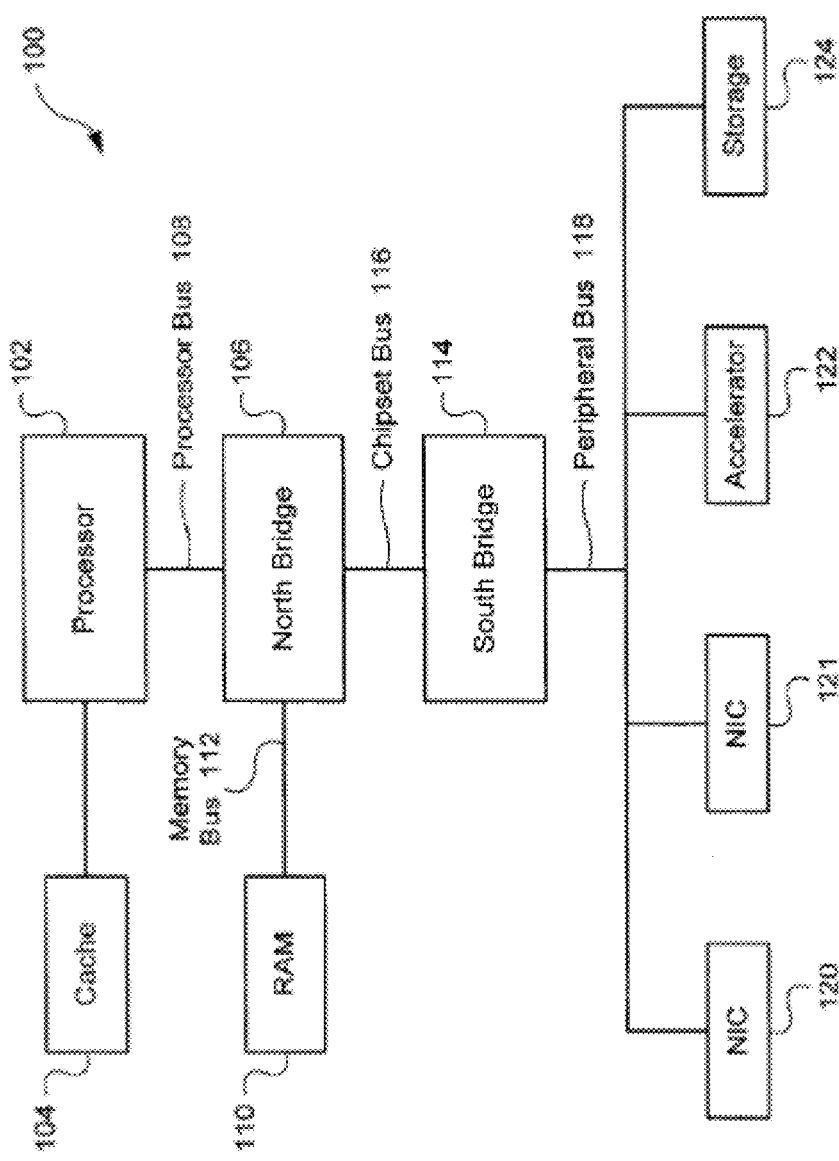
FIG. 22 is a block diagram illustrating a first example architecture of a computer system that can be used in connection with example embodiments of the present invention.

FIG. 22 is a block diagram illustrating a first example architecture of a computer system 100 that can be used in connection with example embodiments of the present invention. As depicted in FIG. 22, the example computer system can include a processor 102 for processing instructions. Non-limiting examples of processors include: the Intel Xeon™ processor, the AMD Opteron™ processor, the Samsung 32-bit RISC ARM 1176JZ(F)-S v1.0™ processor, the ARM Cortex-A8 Samsung S5PC100™ processor, the ARM Cortex-A8 Apple A4™ processor, the Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 22, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MacOS™, BlackBerry OS™, iOS™, and other functionally-equivalent operating systems, as well as application software running on top of the operating system for managing data storage and optimization in accordance with example embodiments of the present invention.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 23:
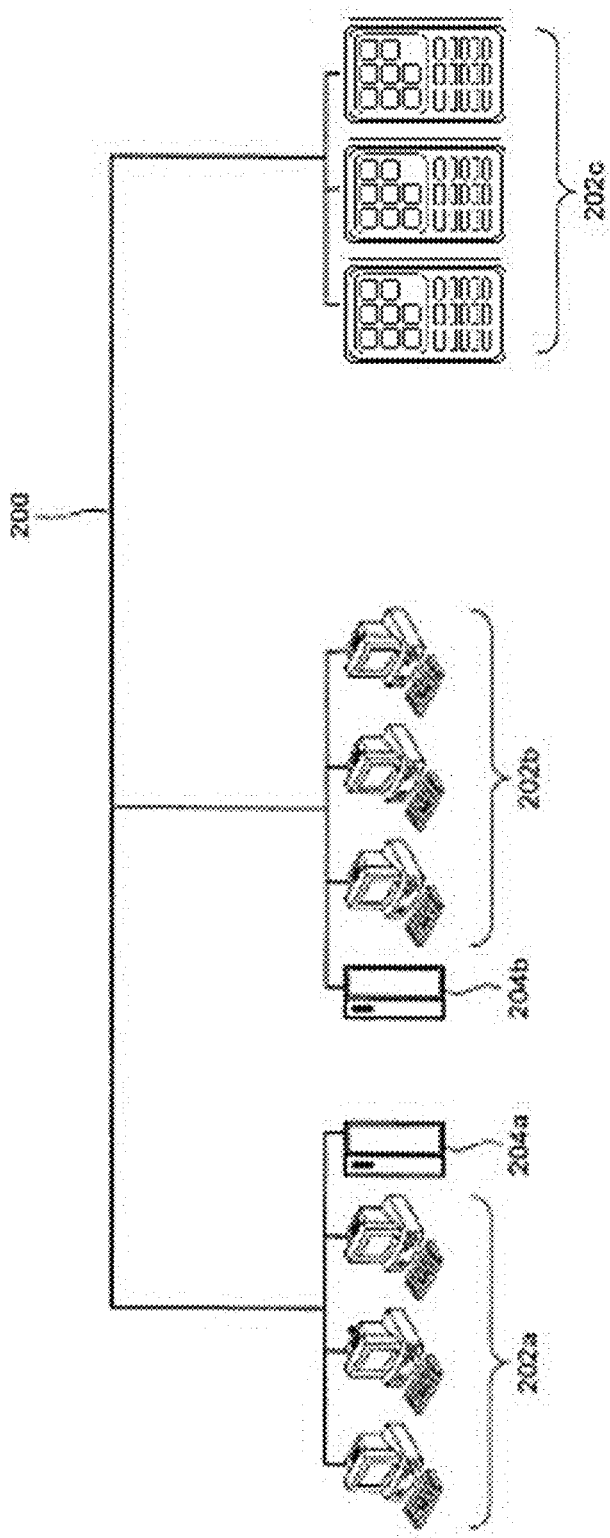
FIG. 23 is a diagram showing one embodiment of a network with a plurality of computer systems, a plurality of cell phones and personal data assistants, and Network Attached Storage (NAS).

FIG. 23 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 23 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 24:
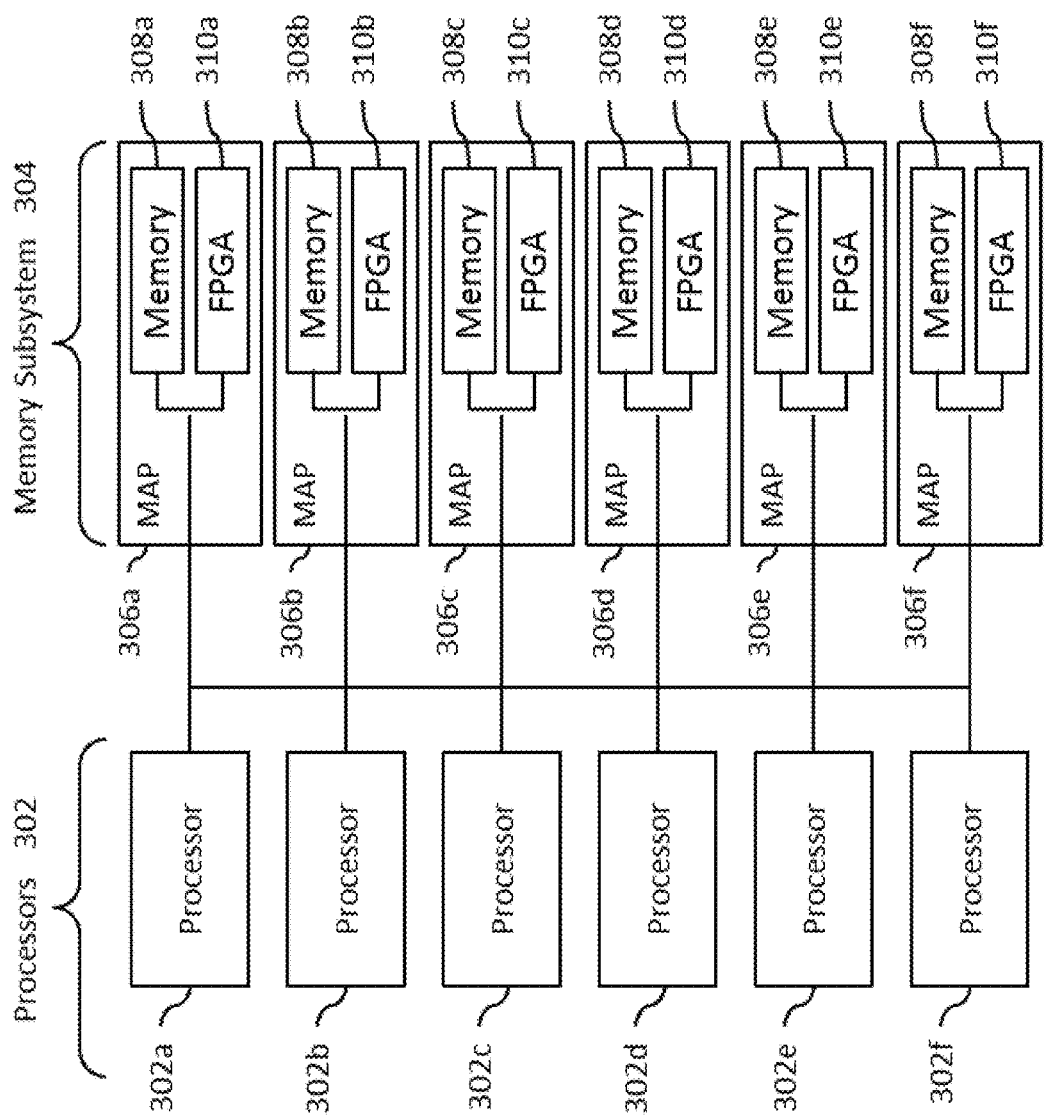
FIG. 24 is a block diagram of a multiprocessor computer system using a shared virtual address memory space in accordance with an example embodiment.

FIG. 24 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 24, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 22.

EXAMPLE 1 (ILLUSTRATIVE)

G-protein coupled receptors (e.g. serotonin, dopamine, glutamate, chemokine, and histamine receptors) are one class of proteins that undergo a conformational change when activated by a ligand, and are thus amenable to study using the present invention. GPCRs that are not intrinsically nonlinear-active may be labeled using a nonlinear active label, and the conformation change is detected via a change in the orientation of the nonlinear active label. One or more labeled GPCR proteins can be attached to a surface, for example by embedding the protein molecules in an array of supported lipid bilayer structures on a glass substrate, where each bilayer structure in the array contains a single species of GPCR molecule. In a preferred embodiment of the present invention, each supported lipid bilayer structure is confined within an individual well of a microplate. The conformation change that results when binding of a ligand activates a GPCR receptor causes a change in the orientation of the label with respect to the optical interface on which the molecules are immobilized, and thus a change in properties of the nonlinear optical beams (e.g., second harmonic light) such as intensity, wavelength or polarization.

In a screening experiment, a microwell plate containing the immobilized GPCRs is positioned on the translation stage mechanism of the high throughput analysis system and moved into position for measuring a signal in a first well. A background signal can be measured for the one or more GPCR samples prior to exposure of the immobilized GPCR molecules to a test compound by measuring the nonlinear optical signal from the first well, repositioning the microwell plate to a second well to repeat the background measurement, and so forth. Repeat measurements of nonlinear optical signals are then made for each well at one (endpoint assay mode) or more (kinetic measurement mode) defined time points following the addition of the test compound, and analyzed to determine if the test compound induced conformational change in the one or more GPCR species.

In some cases, binding of a test compound to a GPCR molecule may lead to a change in measured nonlinear optical properties even though the GPCR is not activated by the test compound. For example, this can be due to an interaction between the test compound and the GPCR molecule in the bound complex which alters the orientation of the attached label with respect to the receptor molecule, rather than a change in the conformation of the receptor molecule. A control can be performed, if desired, to assign measured changes in nonlinear optical properties to binding or activation of the receptor, for example, by using a compound which is known to bind to a given GPCR receptor but not to produce a conformational change. If necessary, the position of the label on the GPCR can be altered by changing the conjugation chemistry of the label and/or genetically modifying the receptor to introduce new labeling sites, in order to ensure that observed changes in nonlinear optical signal correlate to receptor activation or conformational change.

In the example described above, each of the GPCR molecules immobilized in the array of lipid bilayer structures on the glass substrate (and further separated by means of the wells in which they reside) are subjected to measurement and analysis by means of repositioning the glass substrate (microplate) with respect to the excitation light beam through the use of the precision X-Y translation stage, while maintaining efficient optical coupling via the recirculating index-matching fluid, index-matching elastomer, or prism grating designs disclosed above.

Typically, the dispensing of test compound solutions into the wells of the microplate will be performed by a programmable, automated liquid-dispensing unit that is integrated with the optical instrument system. Each of the GPCR species immobilized in the wells of the microplate may be exposed to the same test compound, or each may be exposed to a different test compound. In some aspects of the present invention, the high throughput analysis system will further comprise robotics for moving microwell plates comprising the GPCR samples to be analyzed from an external storage system into a "home" position for the translation stage, or for replacing GPCR-containing microplates for which analysis has been completed with new sample plates. In other aspects of the present invention, the high throughput analysis system will further comprise additional robotics for moving standard microplates containing the collection of test compounds into and out of a "home" position for the liquid-dispensing unit.

In a preferred aspect of the present invention, a computer system (i.e. a processor or controller) is configured to run software for (i) controlling all programmable components of the high throughput analysis system, (ii) synchronizing the operational steps of moving microwell plates into and out of position, taking background optical measurements, dispensing test compound solutions, and repeating the optical measurements for use in end-point or kinetic mode assays, (iii) storing and processing the nonlinear optical signal data received from the detector, and (iv) optimizing the overall throughput of analysis (e.g. in terms of number of GPCR sample/test compound combinations analyzed per hour) by using the input system setup parameters (e.g. number of microwell plates to be analysed, number of wells per plate, number of test compounds to be tested, endpoint versus kinetic measurement mode, etc.) to calculate an optimal order for interspersing background measurement, test compound dispensing, and repeat measurement steps for the different wells on each microplate.

EXAMPLE 2 (MOLD DESIGN & PROCESS FOR FABRICATING PRISM ARRAYS)

Figure 13:
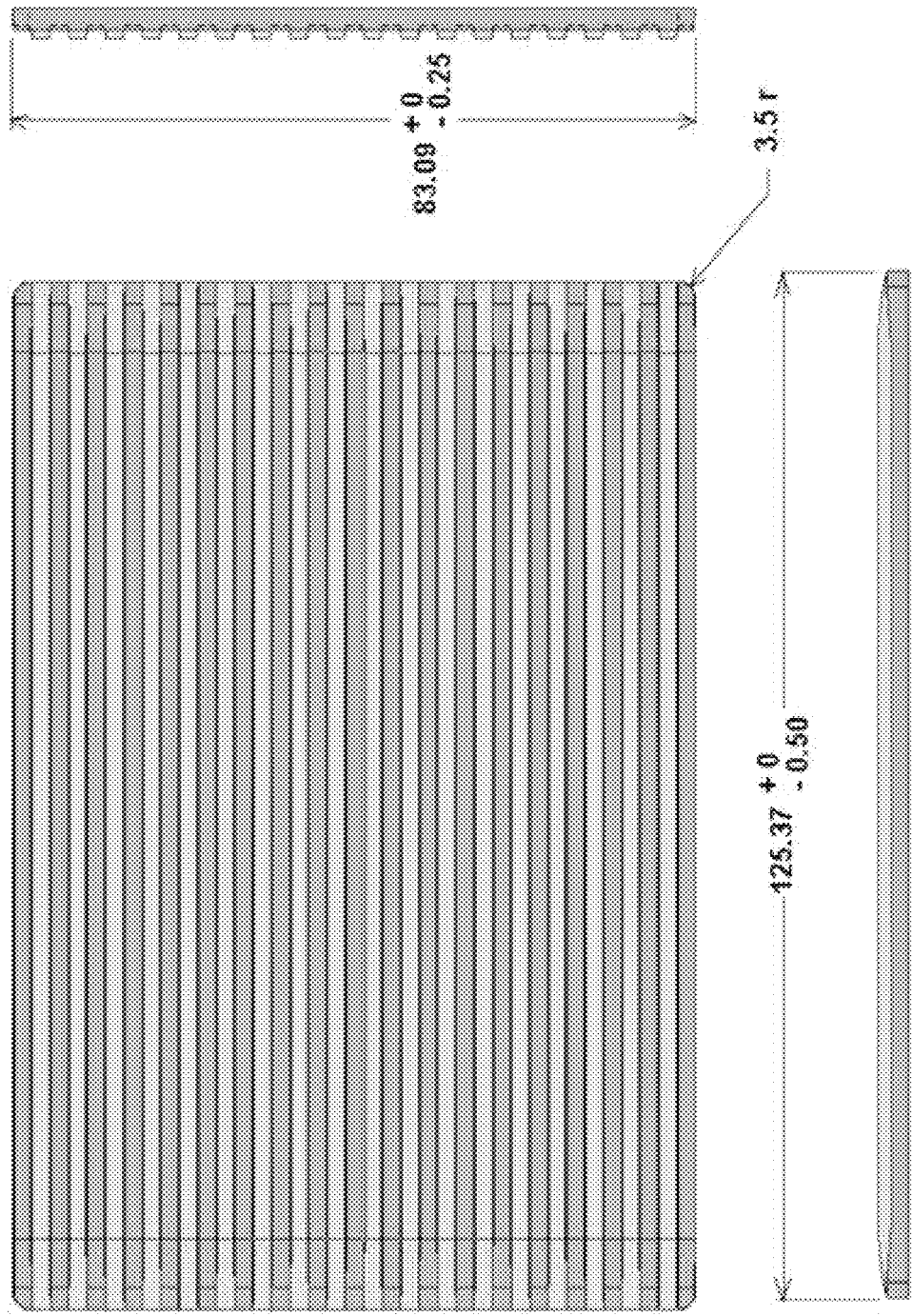
FIGS. 13A-C show one example of a prism array design according to the present disclosure.
Figure 14:
FIG. 14 shows a crossed-polarizer image of a prism array fabricated using a first mold design and first injection molding process. Note the high level of stress-induced birefringence observed.
Figure 15:
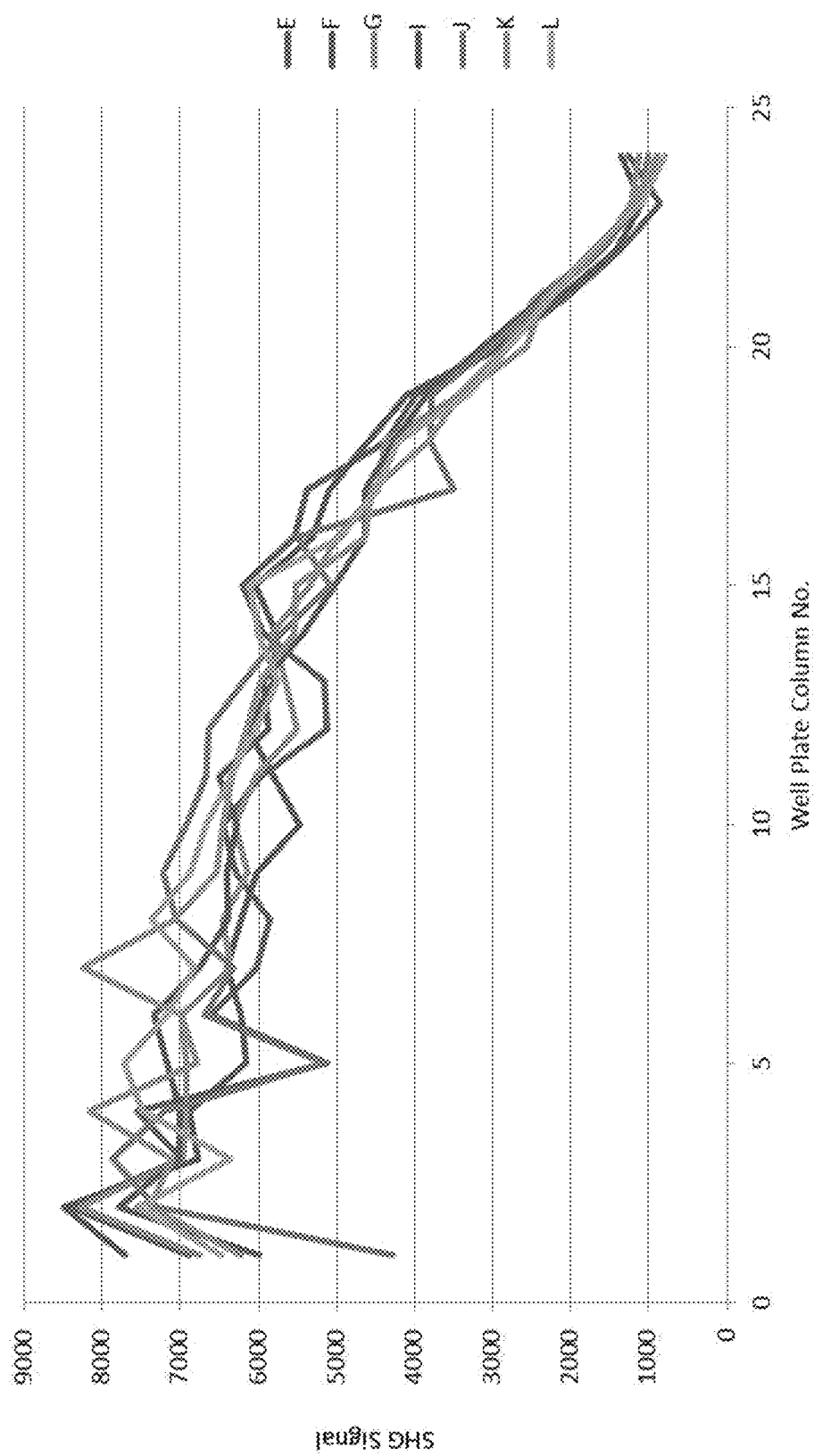
FIG. 15 shows data for the SHG signal intensity measured at different positions in a microwell plate device incorporating the prism array design illustrated in FIGS. 13A-C and FIG. 14. SHG signal intensity was measured for different rows (different traces) as a function of well column number.

A mold was created to fabricate the original "skip-prism" design shown in FIG. 13, with the injection molding process performed by a specialty optical molding house (Apollo Optical, Rochester, N.Y.). The resulting parts show stress birefringence (see the crossed-polarizer image in FIG. 14), and the measured SHG signal is adversely affected by this birefringence (FIG. 15), with the signal dropping along the length of the prism array.

In order to reduce or eliminate the birefringence effect on SHG signal, we experimented with the type of plastic used (COP, COC, acrylic, etc), different molding processing conditions (temperature, pressure, flow rate, cycle time, etc), and post-molding annealing. We were able to find materials and process parameters that reduced the birefringence modestly, but those conditions also tended to cause the plastic part to adhere tightly to the mold and fracture upon release from the mold. (Note: this mold contained ejection devices that pushed only on the vent and gate ends of the part). Annealing the part reduced stress birefringence significantly, but caused excessive mechanical warping of the part thereby making it unusable.

Injection molding flow simulations indicated that stress was created primarily at the transition from the planar gate to the prism-structured part (results not shown). The simulation results also predicted that the part could be made longer than required and then trimmed to length, thereby mechanically removing the stressed regions of the molded part and resulting in a prism array of the same final length as in the original design.

The results of the mold flow simulation were used to design a new mold that includes several significant changes:
1. The overall length of the part has been increased to allow birefringent transition zones to be trimmed off
2. Gate and vent features were made longer to reduce shear stress in the plastic.
3. Mold eject features were added along the length and width of the part to facilitate release from the mold and reduce the chance of fracturing the part during release.
4. "Glue bumps" were added to the planar side of the array to control the thickness of the glue layer when the prism array is laminated to a glass-bottom microplate, and to improve glue adhesion during temperature variation.

Figure 19:
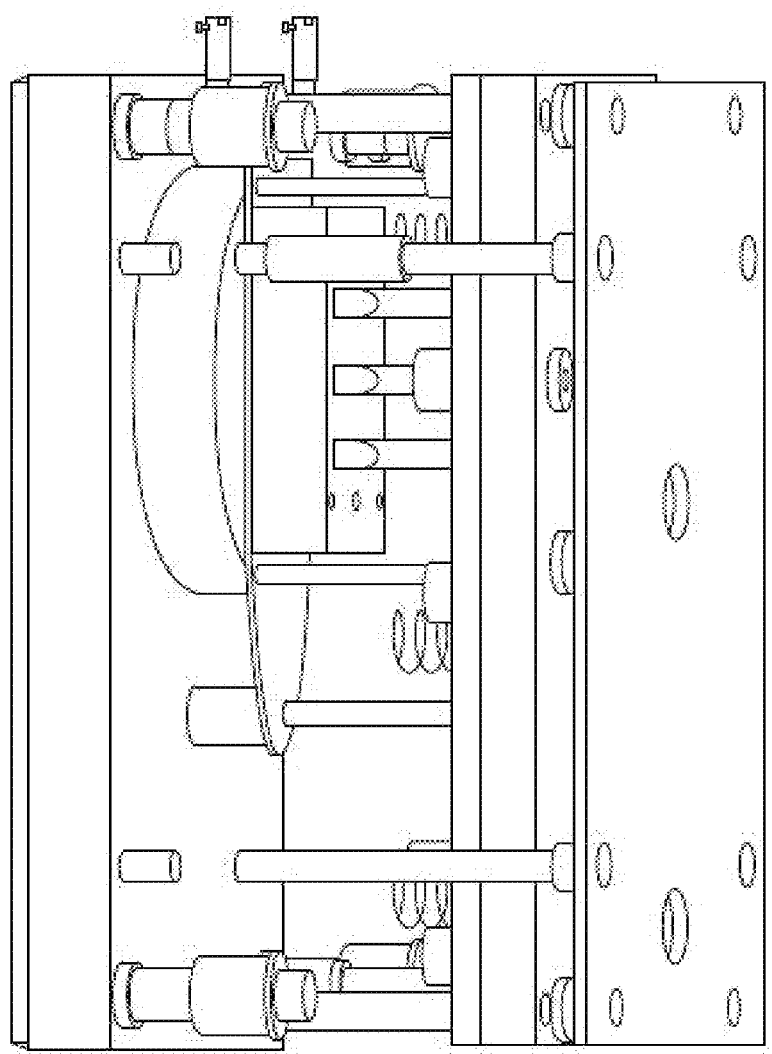
FIG. 19 shows a cut-away version of the mold tool used to fabricate the prism array part illustrated in FIGS. 16A-C.
Figure 20:
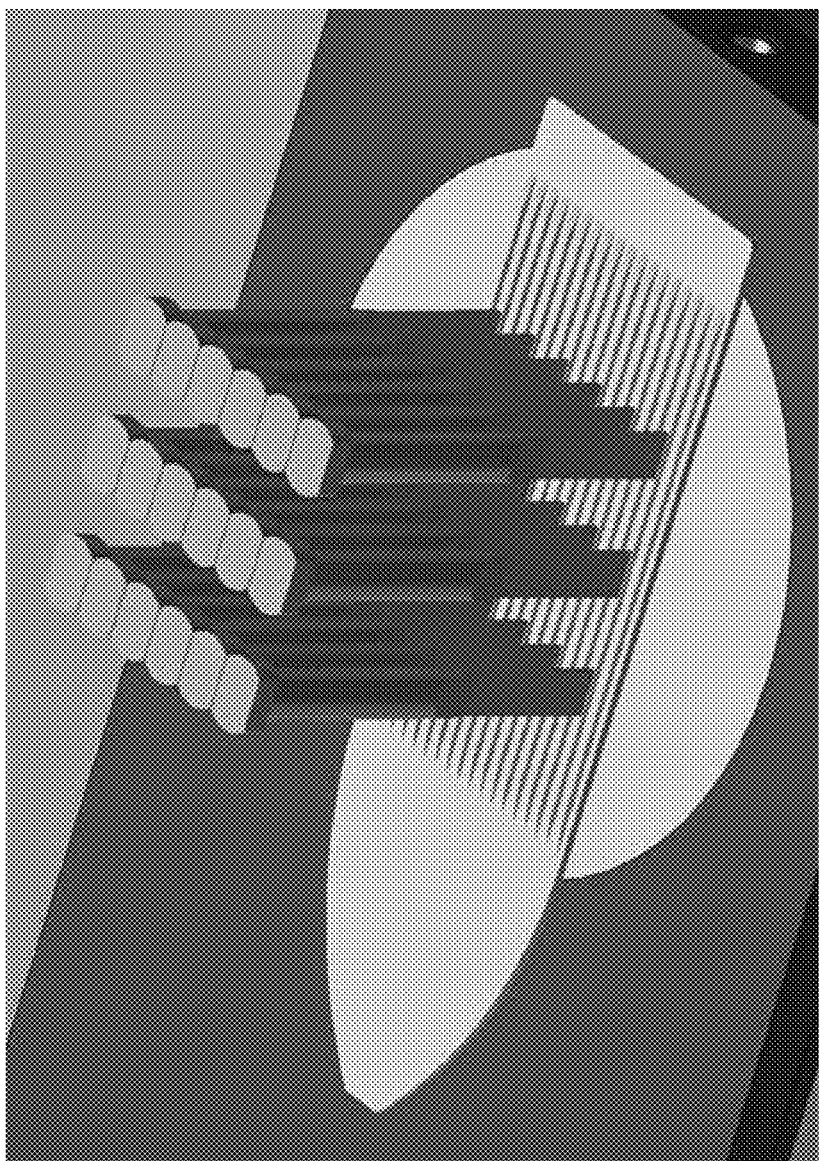
FIG. 20 illustrates the array of blade-like ejection features used in the mold tool for providing uniform pressure on the prism array part during release from the mold.

The new part design is shown in FIG. 16, including the gate (left) and vent (right) features. FIG. 19 shows a cut-away version of the mold tool. Note that there is a 6×3 array of "ejector blade" devices (i.e. "ejection devices") that are used during mold release to apply more uniform pressure to the part during release (FIG. 20). Additional ejection features (not shown) are also used in the gate and vent regions. Generally, optical-quality molded parts do not use ejector features at all since ejectors impact on the surface of the part and can create blemishes. Since our prism array design has some regions that are not optically addressed, we were able to arrange the ejector blades to impact the part only in those regions where optical performance of the part is non-critical.

In general, the larger the number of blade-like ejector features in an m×n array of ejection devices, the more uniform the pressure exerted on the part during mold release. In some embodiments, m and/or n will have a value of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20. In some embodiments, m and/or n will have a value of at most 20, at most 19, at most 18, at most 17, at most 16, at most 15, at most 14, at most 13, at most 12, at most 11, at most 10, at most 9, at most 8, at most 7, at most 6, at most 5, at most 4, at most 3, or at most 2. The values of m and n may the same or may be different, and may include any combination of values within the above-specified range.

Figure 17:
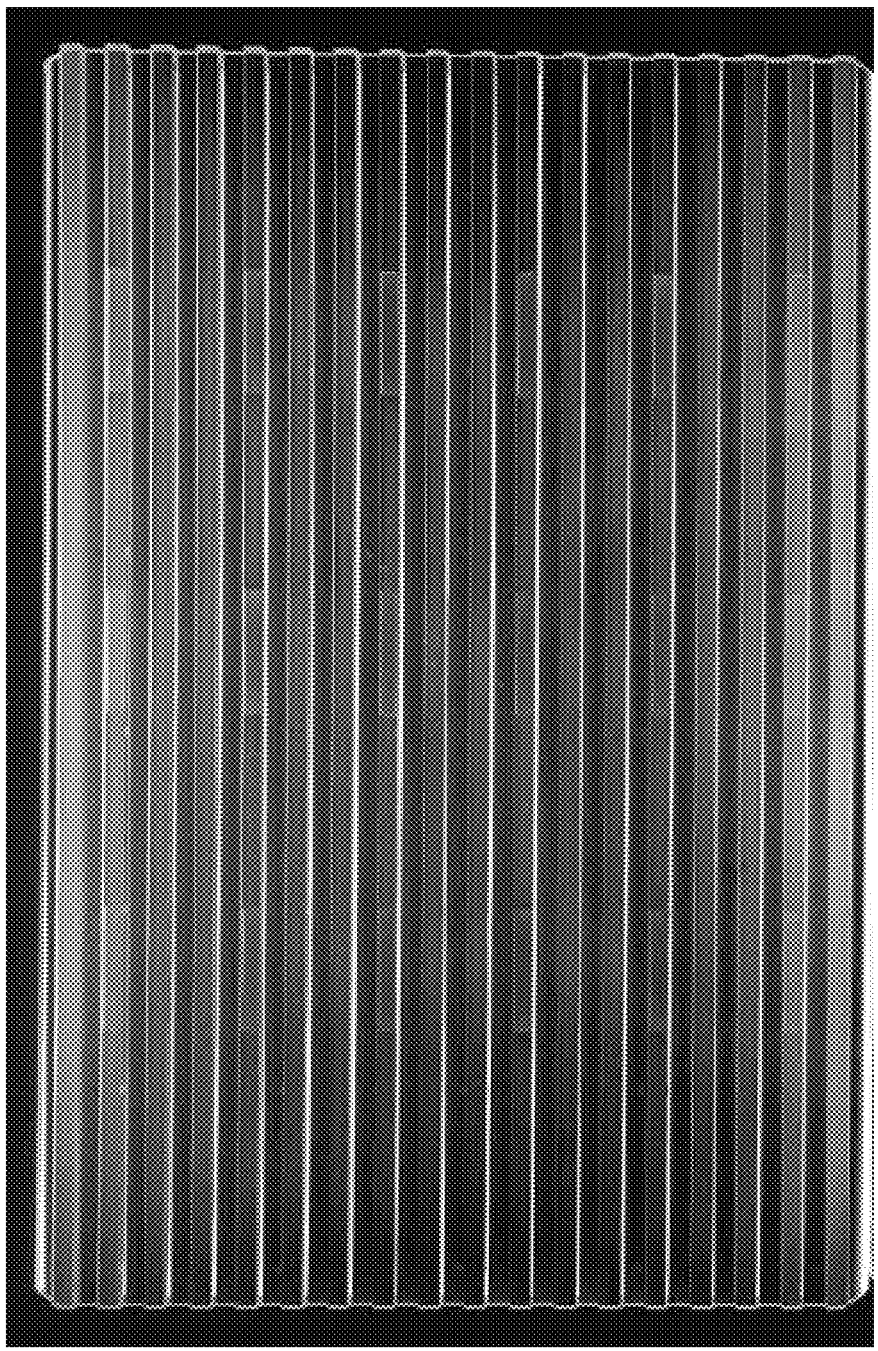
FIG. 17 shows a crossed-polarizer image of a prism array fabricated using an improved mold design and optimized injection molding process. Note that the level of stress-induced birefringence observed is significantly reduced compared to that shown in FIG. 14.
Figure 18:
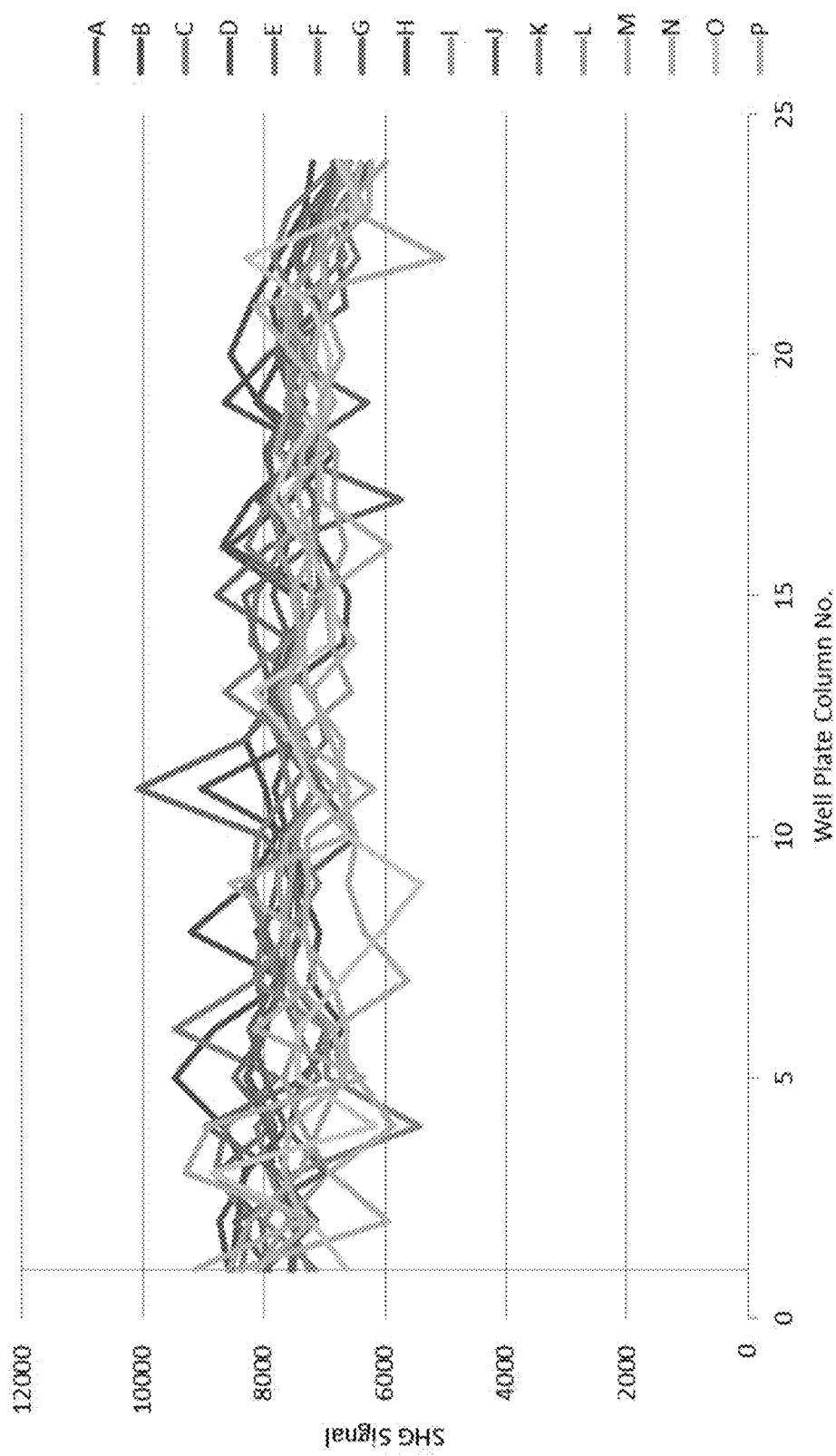
FIG. 18 shows data for the SHG signal intensity measured at different positions in a microwell plate device incorporating the prism array design illustrated in FIGS. 16A-C and FIG. 17. SHG signal intensity was measured for different rows (different traces) as a function of well column number. Note that the level of SHG signal intensity is higher and more uniform across the microwell plate compared to that shown in FIG. 15.

The new mold design, specifically the ejection features, allowed the injection molding vendor to experiment with different pressure and temperature profiles which would have caused release-fracture in the original mold. These conditions effectively de-stress the plastic during the molding process, but cause the part to adhere more tightly to the optical mold surface. The ejector features distributed across the length and width of the part allow the part to be ejected from the mold without fracturing. Prism parts made with new mold have negligible stress birefringence, as shown in the cross-polarizer image in FIG. 17. SHG data also shows a much more uniform signal response along the length of the prism array (FIG. 18). Residual birefringence is still detectable, but the extra length of the part allows us to optimize the trim locations to cut off the transition regions where there is the most birefringence (data not shown).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device comprising:
   a) a substrate, the substrate comprising:
      i) an M×N array of discrete regions on a surface of the substrate, wherein M is the number of rows of discrete regions and N is the number of columns of discrete regions in the array, and
      ii) an R×S array of prisms integrated with the substrate and optically coupled to the discrete regions, wherein R is the number of rows of prisms and S is the number of columns of prisms in the array;
   wherein each discrete region is located directly above a single prism of the array of prisms integrated with the substrate, and wherein R[≠]M and S=N, or R=M and S[≠]N.

2. The device of claim 1, wherein each of the discrete regions is optically coupled with at least one input prism and at least one output prism, and wherein the input prism and the output prism are spatially distinct.

3. The device of claim 1, wherein M=8 and N=12.

4. The device of claim 1, wherein M=16 and N=24.

5. The device of claim 1, wherein M=32 and N=48.

6. The device of claim 1, wherein M is greater than 4 and N is greater than 4.

7. The device of claim 1, wherein each discrete region comprises a supported lipid bilayer or is configured to facilitate the formation of a supported lipid bilayer.

8. The device of claim 1, further comprising a well-forming component bonded to a top surface of the substrate in order to isolate each discrete region in a separate well.

9. The device of claim 1, wherein each of the discrete regions comprises an area of up to about 100 mm$^2$.

10. The device of claim 1, wherein the substrate is composed of glass, fused-silica, or plastic.

11. A device comprising:
    a) a substrate, the substrate comprising:
       i) an M×N array of discrete regions on a surface of the substrate, wherein M is the number of rows of discrete regions and N is the number of columns of discrete regions in the array, and
       ii) an R×S array of prisms integrated with the substrate and optically coupled to the discrete regions, wherein R is the number of rows of prisms and S is the number of columns of prisms in the array;
    wherein each discrete region is located directly above a single prism of the array of prisms integrated with the substrate, and wherein each of the discrete regions is optically coupled with at least one input prism and at least one output prism that are not located directly beneath the discrete region.

12. The device of claim 11, wherein M=8 and N=12.

13. The device of claim 11, wherein M=16 and N=24.

14. The device of claim 11, wherein M=32 and N=48.

15. The device of claim 11, wherein M is greater than 4 and N is greater than 4.

16. The device of claim 11, wherein each discrete region comprises a supported lipid bilayer or is configured to facilitate the formation of a supported lipid bilayer.

17. The device of claim 11, further comprising a well-forming component bonded to a top surface of the substrate in order to isolate each discrete region in a separate well.

18. The device of claim 11, wherein the substrate is composed of glass, fused-silica, or plastic.

* * * * *

UNITED STATES PATENT AND TRADEMARK OFFICE
CERTIFICATE OF CORRECTION

PATENT NO. : 10,451,630 B2  
APPLICATION NO. : 15/965577  
DATED : October 22, 2019  
INVENTOR(S) : Joshua Salafsky et al.

Page 1 of 1

It is certified that error appears in the above-identified patent and that said Letters Patent is hereby corrected as shown below:

In the Claims

Column 27, Claim 1, Lines 45-46:
Replace "and wherein R [≠] M and S = N, or R = M and S [≠] N." with --and wherein R ≠ M and S = N, or R = M and S ≠ N.--

Signed and Sealed this  
Sixth Day of October, 2020

Andrei Iancu  
*Director of the United States Patent and Trademark Office*